United States Patent [19]

Ong et al.

[11] Patent Number: 4,943,571
[45] Date of Patent: Jul. 24, 1990

[54] AMINOALKYLTHIODIBENZOXEPINS AND PHARMACEUTICAL USE

[75] Inventors: Helen H. Ong, Whippany; Vernon B. Anderson, High Bridge, both of N.J.; James A. Profitt, Goshen, Ind.

[73] Assignee: Hoechst-Roussel Phamraceuticals Inc., Somerville, N.J.

[21] Appl. No.: 335,354

[22] Filed: Apr. 10, 1989

Related U.S. Application Data

[60] Division of Ser. No. 738,507, May 28, 1985, Pat. No. 4,837,227, which is a continuation of Ser. No. 330,257, Dec. 14, 1981, abandoned, which is a continuation-in-part of Ser. No. 226,045, Jan. 19, 1981, abandoned, which is a continuation of Ser. No. 29,462, Apr. 12, 1979, abandoned, which is a continuation-in-part of Ser. No. 860,083, Dec. 13, 1977, abandoned.

[51] Int. Cl.$^5$ .................. H61K 31/35; H61K 31/585; C07D 311/80; C07D 413/12
[52] U.S. Cl. .................. 514/232.8; 514/253; 514/320; 514/422; 514/450; 544/150; 544/375; 546/196; 548/525; 549/354
[58] Field of Search ............. 549/354; 514/450, 232.8, 514/253, 320, 422; 544/150, 375; 546/196; 548/525

[56] References Cited

PUBLICATIONS

Protiva et al., It Farmaco, vol. 20 (1966), pp. 721–725.

*Primary Examiner*—Richard L. Raymond
*Attorney, Agent, or Firm*—Raymond R. Wittekind

[57] ABSTRACT

Novel aminoalkylthiodibenzoxepins, physiologically tolerable acid addition salts thereof, a method of preparing same, pharmaceutical and veterinary preparations including same and methods of treating by administering same are disclosed. These compounds are useful as analgesic, antidepressant and anticonvulsant agents. A process for selectively reducing olefins by alkaline earth metals in loweralkanols is also disclosed.

39 Claims, No Drawings

AMINOALKYLTHIODIBENZOXEPINS AND PHARMACEUTICAL USE

This is a division of application Ser. No. 738,507 filed May 28, 1985, now U.S. Pat. No. 4,837,227, which is a continuation of application Ser. No. 330,257 filed Dec. 14, 1981 now abandoned which is a continuation-in-part of application Ser. No. 226,045 filed Jan. 19, 1981, now abandoned, which is a continuation of application Ser. No. 029,462 filed Apr. 12, 1979, now abandoned, which is a continuation-in-part of application Ser. No. 860,083 filed Dec. 13, 1977, now abandoned.

This invention relates to novel aminoalkylthiodibenzoxepins and to their physiologically tolerable acid addition salts which are useful as analgesic, antidepressant and anti-convulsant agents, to a method of treatment with pharmaceutically effective amounts thereof and to pharmaceutical and veterinary compositions containing such a compound as an essential active ingredient.

To the best of our knowledge, the compounds of this invention have not heretofore been described or suggested. Amethoclothepine of the formula

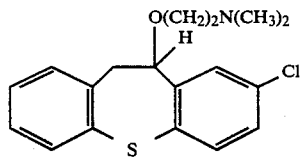

is reported to possess central depressant activity by M. Protvia, et al. II Farmaco XXI, 98 (1966).

Japanese Patent No. 47-28998 entitled "A Method of Manufacturing Tricyclic Compounds Having an Enolic Ether Bond" pertains to the preparation of compounds depicted by the formula

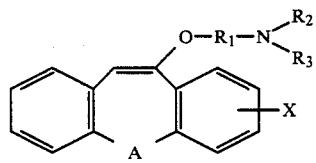

in which A is alkylimino, oxy, thio or sulfinyl, $R_1$ is alkylene, $R_2$ and $R_3$ each represent an alkyl group or may be bonded cyclically either through an alkylimino group or not through an alkylimino group and X stands for hydrogen, halogen, alkyl, alkoxy, alkylthio, dialkyl sulfamoyl or nitro.

The compounds of the present invention conform to the general formula

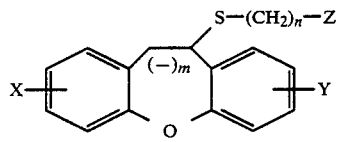

wherein X and Y are the same or different and each can be hydrogen, halogen, trifluoromethyl, loweralkoxy, loweralkyl, loweralkylthio, loweralkylsulfonyl, loweralkylsulfinyl, amino, or nitro; Z is halogen or

$R^1$ is hydrogen, straight or branched chain loweralkyl, cyano, cycloalkylloweralkyl wherein the cycloalkyl ring contains from 3 to 6 carbon atoms, phenoxycarbonyl of the formula

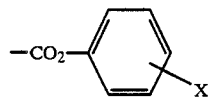

where X is defined as above, alkoxycarbonyl, loweralkenyl or loweralkynyl; $R^2$ is straight or branched chain loweralkyl or cycloalkylloweralkyl wherein the cycloalkyl ring contains from 3 to 6 carbon atoms; phenylethyl of the formula

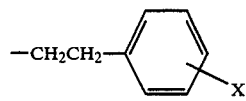

wherein X is defined as above, loweralkenyl or loweralkynyl; and when $R^1$ and $R^2$ are taken together with the nitrogen atoms to which they are attached, the group $R^1$—N—$R^2$ forms a heterocycle which is morpholino, piperidino, 4-substituted piperidino in which the 4-substituent is benzoyl of the formula

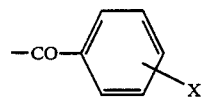

wherein X is defined as above, pyrrolidinyl, piperazinyl or N-substituted piperazinyl in which the N-substituent is loweralkyl and in which a nitrogen or carbon atoms of the heterocycle is attached to the terminal carbon atoms of the ($CH_2$) group; m is the integer 0 or 1; and n is an integer of from 2 to 4; and a physiologically tolerable acid addition salt thereof.

In the above definitions, the term lower means the group it is describing contains from 1 to 6 carbon atoms.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, and oxalic acids.

Compounds of the invention are prepared by one of the several methods given below. With the exception noted, X,Y,Z,$R^1$,$R^2$, m and n are as defined earlier.

Method A

A 10,11-dihydro-10-hydroxydibenz[b,f]oxepin, of the formula

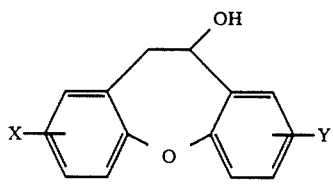

is reacted with aminoalkylthiol of the formula

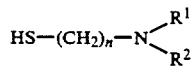

wherein $R^1$ and $R^2$ are the same or different and each can be straight or branched chain loweralkyl to produce a compound of the invention of the formula

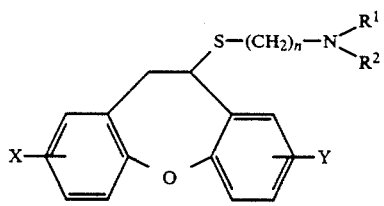

This reaction is carried out with a catalyst/dehydrating agent of boron trifluoride etherate and in the presence of a suitable solvent such as glacial acetic acid at a temperature of about ambient to reflux.

Method B

A 10,11-dihydro-10-oxodibenz[b,f]oxepin of the formula

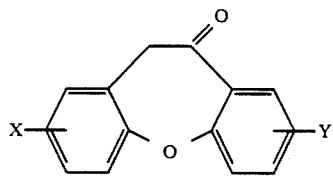

is treated in a manner similar to Method A to obtain a compound of the invention of the formula

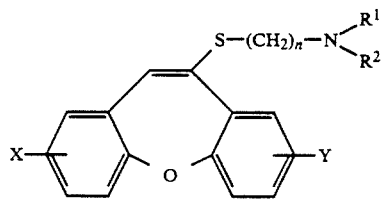

Method C

A compound prepared in Method B can be treated with magnesium in a suitable solvent to effect reduction to its corresponding saturated aminoalkylthiodibenzoxepin. A preferred method of carrying out this reduction involves the use of magnesium shavings with a solvent of methanol. The more general process of which Method C is a part is described supra.

Method D

A compound prepared in Method A, B or C, wherein $R^1$ and $R^2$ are each methyl, can be treated with a cyanogen halide such as cyanogen bromide in a suitable solvent and acid scavenger to obtain a mixture of one compound of the invention of the formula

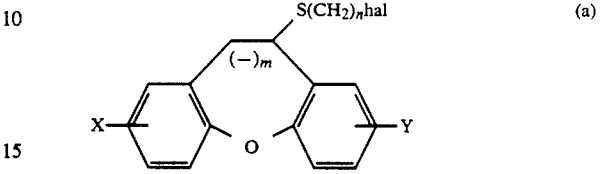

and another compound of the invention of the formula

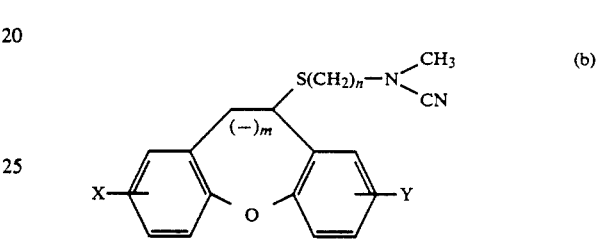

This reaction is carried out at a temperature of from about ambient to reflux. These two compounds of the invention may be isolated and collected by column chromatography.

Method E

A compound prepared in Method D of formula (a) can be reacted in a known fashion with a suitable amine to obtain the corresponding compound of the invention of the formula

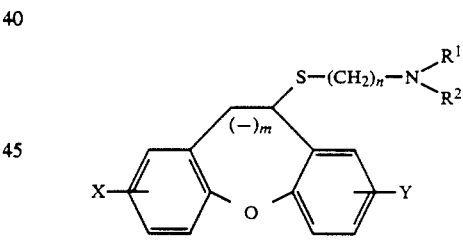

wherein $R^1$ is hydrogen, straight or branched chain loweralkyl, cycloalkylloweralkyl, loweralkenyl or loweralkynyl; $R^2$ is straight or branched chain loweralkyl or cycloalkylloweralkyl wherein the cycloalkyl ring contains 3 to 6 carbon atoms, phenylethyl of the formula

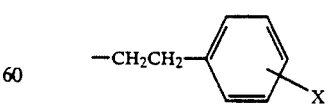

wherein X is as defined above, loweralkenyl or loweralkynyl; and when $R^1$ and $R^2$ are taken together with the nitrogen atom to which they are attached, the group $R^1$—N—$R^2$ forms a heterocycle which is piperazinyl, N-substituted piperazinyl in which the N-substituent is loweralkyl, morpholino, piperidino, 4-substituted piperidino in which the 4-substituent is benzoyl of the formula

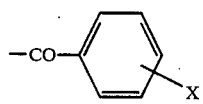

wherein X is defined as above or pyrrolidinyl. A preferred method is carried out with a dimethylformamide solvent, a catalyst such as sodium bicarbonate and a reaction initiator such as potassium iodide at a temperature of from ambient to the reflux temperature of the reaction mixture.

Method F

A compound prepared in Method A, B or C can be treated with a chloroformate, e.g. an alkyl or phenyl chloroformate, at a temperature of from 25° to 125° C., in a solvent such as methylene chloride, toluene or benzene to provide the corresponding compound of the invention in which Z is

with $R^1$ being alkoxy- or phenoxy-carbonyl.

Method G

A compound prepared in Method F is treated with an organic base such as triethylamine or an inorganic base such as sodium or potassium hydroxide in a solvent such as water, ethanol or ethylene glycol at a temperature of from ambient to reflux to provide the corresponding compound of the invention in which $R^1$ is hydrogen.

Method H

A compound prepared in Method G is treated with a straight or branched chain loweralkyl halide, loweralkenyl, halide, loweralkynyl halide or cycloalkylloweralkyl halide under conditions normal for such reactions to provide the corresponding compound of the invention in which $R^1$ is straight or branched chain loweralkyl, loweralkenyl, lower-alkynyl or cycloalkylloweralkyl. A preferred method is to carry out this substitution in the presence of a solvent such as dimethylformamide, an acid scavenger such as sodium bicarbonate and a reaction initiator such as potassium iodide at the reflux temperature of the solvent.

Further to and in continuation of the disclosure of a method of reducing dibenz[b,f]oxepines to 10,11-dihydrodiben[b,f]oxepins (Method C, supra), the present invention relates more generally to a process for selectively reducing one or more partially substituted aliphatic or pseudoaromatic carbon-to-carbon double bond of a compound, including a dibenz[b,f]oxepin, selected from the group consisting of olefins of the formula

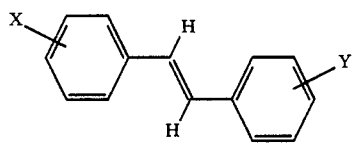

wherein X and Y are the same or different and each can be hydrogen, halogen, trifluoromethyl, loweralkoxy, loweralkyl, loweralkylthio, or amino,

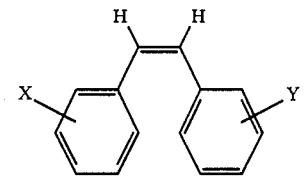

wherein X and Y are as above,

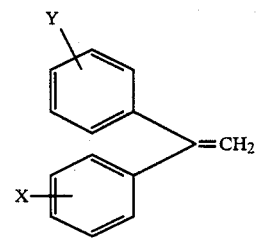

wherein X and Y are as above and

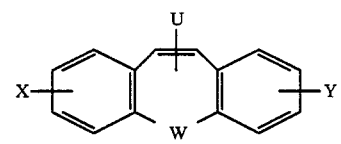

wherein X and Y are as above; U is hydrogen, amino, disubstituted amino in which the substituents are straight or branched chain loweralkyl, N-substituted piperazinyl in which the N-substituent is straight or branched chain loweralkyl or a group of the formula —V—$(CH_2)_m$—Z wherein V is imino, oxy or thio, m is an integer of from 2 to 4 and Z is halogen or

$R^1$ is hydrogen, straight or branched chain loweralkyl, cyano, cycloalkylloweralkyl wherein the cycloalkyl ring contains 3 to 6 carbon atoms, phenoxycarbonyl of the formula

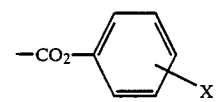

where X is defined as above, alkoxycarbonyl, loweralkenyl or loweralkynyl; $R^2$ is straight or branched chain loweralkyl or cycloalkylloweralkyl wherein the cycloalkyl ring contains from 3 to 6 carbon atoms, phenylethyl of the formula

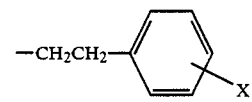

wherein X is defined as above, alkoxycarbonyl, loweralkenyl or loweralkynyl; and where $R^1$ and $R^2$ are taken together with the nitrogen atom to which they are attached, the group $R^1$—N—$R^2$ forms a heterocycle which is morpholino, piperidino, 4-substituted piperidino in which the 4-substituent is benzoyl of the formula

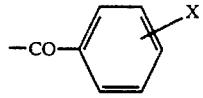

wherein X is defined as above, pyrrolidinyl, piperiazinyl or N-substituted piperazinyl in which the N-substituent is loweralkyl; and W is imino, oxy, thio, methylene, a group of the formula

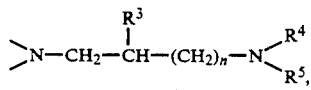

wherein $R^3$ is hydrogen or straight or branched chain loweralkyl; $R^4$ and $R^5$ are each independently hydrogen or straight or branched chain loweralkyl; and where $R^4$ and $R^5$ are taken together with the nitrogen atom to which they are attached, the group $R^4$—N—$R^5$ form a heterocycle which is piperazinyl or N-substituted piperazinyl in which the N-substituent is hydrogen, straight or branched chain loweralkyl or hydroxy straight or branched chain loweralkyl and n is 0 to 2; a group of the formula

wherein $R^6$ is hydrogen or hydroxy and $R^7$ is

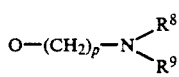

wherein $R^8$ and $R^9$ are each independently hydrogen or straight or branched chain loweralkyl; and wherein $R^8$ and $R^9$ are taken together with the nitrogen atom to which they are attached, the group $R^8$ N—$R^9$ forms a heterocycle which is N-substituted piperazinyl in which the N-substituent is straight or branched chain loweralkyl and p is 0 to 3;

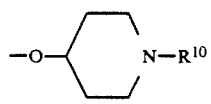

wherein $R^8$ and $R^9$ are as above and p is 2 to 3;

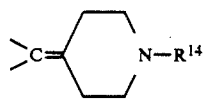

wherein $R^{10}$ is straight or branched chain loweralkyl;

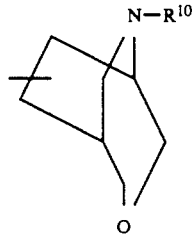

wherein $R^{10}$ is as above and p is 2 to 3; or

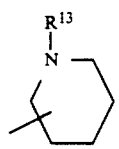

wherein $R^{10}$ is as above; a group of the formula $>C=CH-(CH_2)_q-T$ wherein T is $$-N\begin{matrix}R^{11}\\R^{12}\end{matrix}$$

wherein $R^{11}$ and $R^{12}$ each indepent are hydrogen, straight or branched chain loweralkyl; and wherein $R^{11}$ and $R^{12}$ are taken together with the nitrogen atom to which they are attached, the group $R^{11}$—N—$R^{12}$ forms a heterocycle which is piperazinyl, 4,4-disubstituted piperidino in which the 4-substituents are phenyl and alkoxycarbonyl or

[structure with $R^{13}$ on N of piperidine ring]

wherein $R^{13}$ is straight or branched chain loweralkyl; and q is an integer of 1 to 3; or a group of the formula

[structure: $>C=$ piperidine $N-R^{14}$]

wherein $R^{14}$ is hydrogen, straight or branched chain loweralkyl or cyclopropylloweralkyl which comprises contacting the olefin with an alkaline earth metal and a loweralkanol to afford a reduced derivative thereof.

Subgeneric to the process for selectively reducing one or more partially substituted aliphatic or pseudoaromatic carbon-to-carbon double bonds of olefins are those processes in which the olefinic component is selected from the group consisting of trans-stilbene, cis-stilbene, 1,1-diphenylethyler 5H-dibenz[b,f]azepin, 1-loweralkyl-4-(5-dibenzo[a,d]cycloheptenylidene)-piperidine, phenanthrene and thioenolether of the formula

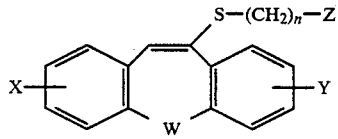

wherein X and Y are the same or different and each can be hydrogen, halogen, trifluoromethyl, loweralkoxy, loweralkyl, loweralkylthio or amino; Z is halogen or

$R^1$ is hydrogen, straight or branched chain loweralkyl, cyano, cycloalkylloweralkyl wherein the cycloalkyl ring contains 3 to 6 carbon atoms, phenoxycarbonyl of the formula

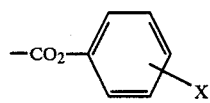

where X is defined as above, alkoxycarbonyl, loweralkenyl or loweralkynyl; $R^2$ is straight or branched chain loweralkyl or cycloalkylloweralkyl wherein the cycloalkyl ring contains from 3 to 6 carbon atoms, phenylethyl of the formula

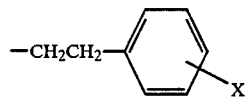

wherein X is defined as above, alkoxycarbonyl, loweralkenyl or loweralkynyl; and where $R^1$ and $R^2$ are taken together with the nitrogen atom to which they are attached, the group $R^1$—N—$R^2$ forms a heterocycle which is morpholino, piperidino or 4-substituted piperidino in which the 4-substituent is benzoyl of the formula

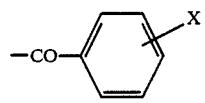

wherein X is defined as above, pyrrolidinyl, piperazinyl or N-substituted piperazinyl in which the N-substituent is loweralkyl; W is oxy or thio; and n is an integer of from 2 to 4 with an alkaline earth metal and a loweralkanol to afford a reduced derivative thereof.

The reduction is conveniently performed by dissolving or suspending a compound containing one or more partially substituted aliphatic or pseudo-aromatic carbon-to-carbon double bonds in a loweralkanol, adding an alkaline earth metal in suitable form and allowing the reaction to proceed for a period, of time necessary for the substantial reduction of the double bond. Appropriate alkaline earth metals include magnesium, calcium, strontium and barium. Magnesium is preferred. Appropriate lower-alkanols include those having from 1 to 6 straight or branched chained carbon atoms such as, for example, methanol, ethanol, 1-propanol, 2-propanol, 2-methyl-2-propanol, pentanol, 3-methyl-3-pentanol and the like. Methanol is preferred. Suitable forms of the alkaline earth metal include pellets, grindings, shavings and the like. Shavings are preferred.

While the reaction temperature is not narrowly critical, it is desirable to perform the reaction at a temperature such that the reduction proceeds at a reasonable rate. Reaction temperatures between about ambient (25° C.) and about 50° C. accomplish this object. However, compounds characterized by the presence of a pseudoaromatic carbon-to-carbon double bond generally require a somewhat higher reaction temperature to reduce the double bond at a convenient rate. For example, to reduce the 9,10-double bond of phenanthrene at a reasonable rate, it is preferred to perform the reduction at the boiling point of the reaction mixture, i.e., at about 65° C. in the case of methanol.

The stilbenes, diphenylethylenes and phenanthrenes of the present process invention are readily available from commercial sources or preparable by methods well known in the art as described generally in standard texts such as "Synthetic Organic Chemistry," R. B. Wagner and H. D. Zook, John Wiley and Sons, John Wiley and Sons, Inc., New York, N.Y., 1953.

The diphenylethanes, obtained by the alkaline earth-loweralkanol reduction process, are useful as solvents and stabilizers.

The 10-(or 11-)substituted 10,11-dihydrodibenz[b,f]oxepins prepared by the alkaline earth metal-loweralkanol reduction process as described herein, are useful as antidepressants, analgesics and anticonvulsants and/or as intermediates for the preparation of such therapeutically valuable agents. The corresponding 10-(or 11-)substituted -10,11-dihydrodibenz[b,f]thiepines, obtained by application of the aforementioned reduction process, also are antidepressants, analgesics and anticonvulsants and/or are convertible into compounds showing such useful properties. See pending U.S. patent application Ser. No. 860,082, filed Dec. 13, 1977. Generally, the synthesis of the precursor tricyclic olefins of the instant invention, i.e., the dibenz[b,f]oxepins, dibenz[b,f]thiepins, dibenz[b,f]azepines and dibenzocycloheptenes and the utility of the reduced products, i.e., the 10,11-dihydrodibenz[b,f]oxepins, 10,11-dihydrodibenz[b,f]thiepines, 10,11-dihydrodibenz[b,f]azepines and 10,11-dihydrodibenzocycloheptenes, as antipsychotics, antidepressants and antiallergenics, are described in "Medicinal Chemistry," A. Burger, Ed., 3rd Ed., Part II, Wiley-Interscience, New York, N.Y. 1970, chapters 54, 55 and 65, inter alia, and references contained therein.

As used herein, the term "partially substituted" as applied to a carbon-to-carbon double bond refers to such a moiety characterized by the presence of 1 to 3 carbon-to-hydrogen bonds. Examples of partially substituted carbon-to-carbon double bonds are the 1,2-double bonds of 1,1-diphenylethylene and cis- and trans-stilbene, the 10,11-double bonds of dibenz[b,f]oxepin, loweralkyl-4-(5-dibenzo[a,d]cycloheptenylidene, dibenz[b,f]thiepin and the 9,10-double bond of phenanthrene. The term "pseudoaromatic" as applied to a carbon-to-carbon double bond refers to such a moiety which, while part of a cyclic aromatic system, exhibits properties characteristic of aliphatic double bond. The 9,10-double bond of phenanthrene is an example of a pseudoaromatic moiety.

Method I

A compound prepared in any of the above methods, which includes a nitro group can be reduced by a conventional method to produce the corresponding amino compound. Such conventional methods include but are not limited to use of metallic zinc and acetic acid or platinum on carbon.

As is appreciated by those skilled in the art, specific conditions in any of the above methods are dependent and are a function of the ingredients of each procedure.

The compounds of the present invention are useful in the treatment of depression in mammals, as demonstrated by their ability to inhibit tetrabenazine-induced depression in mice [International Journal of Neuropharmacology 8, 73 (1969)], a standard assay for useful antidepressant properties. Thus, for instance, the intraperitoneal dose at which the following compounds effect a 50% inhibition of the ptosis of the tetrabenazine-induced depression ($ED_{50}$) in mice are:

| Compound | $ED_{50}$ mg/kg |
| --- | --- |
| 2-fluoro-11-[β-(methylamino)ethylthio]dibenz[b,f]oxepin maleate | 0.3 |
| 10-[β-(methylamino)ethylthio]dibenz[b,f]oxepin oxalate | 3.4 |
| 2-chloro-10,11-dihydro-11-[(β-dimethylamino)ethylthio]dibenz[b,f]oxepin oxalate | 3.5 |
| 2-fluoro-11-[β-(dimethylamino)ethylthio]dibenz[b,f]oxepin hydrobromide | 4.3 |
| 10,11-dihydro-10-[(β-dimethylamino)ethylthio]dibenz[b,f]oxepin oxalate | 7.0 |
| 2-fluoro-10,11-dihydro-11-[β-(dimethylamino)ethylthio]dibenz[b,f]oxepin oxalate | 7.6* |

*oral dose

These data illustrate that the compounds of the invention are useful in the treatment of depression in mammals when administered in an amount ranging from 0.1 to 50 mg per kg of body weight per day.

Compounds of the invention are further useful as analgesic agents due to their ability to alleviate pain in mammals. The analgesic utility of compounds of this invention is demonstrated in the phenyl-p-quinone writhing assay in mice, a standard assay for analgesia [Proc. Soc. Exptl. Biol Med., 95 729 (1957)]. Thus for instance, the subcutaneous dose effecting an approximately 50% inhibition of writhing ($ED_{50}$) in mice produced in this assay is as follows:

| Compound | $ED_{50}$ mg/kg |
| --- | --- |
| 2-fluoro-10,11-dihydro-11-[β-(dimethylamino)ethylthio]dibenz[b,f]oxepin oxalate | 1.9 |
| 2-fluoro-11-[β-(methylamino)ethylthio]dibenz[b,f]oxepin maleate | 2.3 |
| 10-[β-(methylamino)ethylthio]dibenz[b,f]oxepin oxalate | 2.3 |

These data illustrate that the compounds of this invention are useful for the alleviation of pain in mammals when administered in an amount ranging from 0.1 to about 50 mg per kg of body weight per day.

Compounds of the present invention are still further useful as anticonvulsant agents for mammals, as determined by the method of Woodbury, L. A. and Davenport, V. D., in Arch. Int. Pharmacodynam, Vol. 92. (1952) at pages 97 to 107. Thus, for instance, the following intraperitoneal doses at which an approximately 50% protective ($ED_{50}$) from the effect of supramaximal electro shock in mice are:

| Compound | $ED_{50}$ mg/kg |
| --- | --- |
| 10,11-dihydro-10-[β-(dimethylamino)ehylthio-dibenz[b,f]oxepin oxalate | 7.7 |
| 2-fluoro-10,11-dihydro-11-[β-(dimethylamino)ethylthio]dibenz[b,f]oxepin oxalate | 9.0 |
| 2-fluoro-11-[β-(dimethylamino)ethylthio]dibenz[b,f]oxepin hydrobromide | 9.2 |
| 2-fluoro-11-[β-(methylamino)ethylthio]dibenz[b,f]oxepin maleate | 9.9 |
| 2-chloro-10,11-dihydro-11-[β-(dimethylamino)ethylthio]dibenz[b,f]oxepin oxalate | 19.4 |
| 10-[β-(methylamino)ethylthio]dibenz[b,f]oxepin oxalate | 21 |

These data illustrate the utility of compounds of the invention for the treatment of convulsion in mammals when administered in an amount ranging from about 0.1 to 100 mg per kg of body weight per day.

Compounds of the present invention are essentially devoid of central nervous system depressant (neuroleptic) activity as determined in the apormorphine induced climbing mice assay, a standard test for central nervous system depressant (neuroleptic) activity described in Example 55.

Compounds of the present invention exhibit a combination of antidepressant activity as determined in the hereinbefore-described inhibition of tetrabenezine induced ptosis in mice and analgesic activity as determined in the hereinbeforedescribed phenyl-p-quinone writhing assay in mice and the modified D'Amour-Smith analgesia (tail flick) assay, a standard test for analgesic activity described in Example 56.

Other examples of compounds of the invention include:

11-[γ-(dimethylamino)propylthio]-2-ethylsulfonyldibenz[b,f]oxepin;

11-[β-(bromoethyl)thio]-2-methoxy-10,11-dihydrodibenz[b,f]oxepin;

2-ethyl-11-[β-(methylamino)ethylthio]dibenz[b,f]oxepin;

11-[β-(ethylmethylamino)ethylthio]-2-methylsulfinyldibenz[b,f]oxepin;

10,11-dihydro-10-[β-(piperidino)ethylthio]dibenz[b,f]oxepin;

10,11-dihydro-10-[γ-(piperazinyl)propylthio]dibenz[b,f]oxepin;

10,11-dihydro-10-[δ-(piperidino)-n-butylthio]dibenz[b,f]oxepin; (δ referring to position on piperidino ring);

10-[β-(pyrrolidino)ethylthio]dibenz[b,f]oxepin;

3-chloro-10-[β-(ethylmethylamino)ethylthio]dibenz[b,f]oxepin;

10-[β-(ethylamino)ethylthio]10,11-dihydro-4-nitrodibenz[b,f]oxepin;

8-chloro-10,11-dihydro-10-[β-(dimethylamino)ethylthio]-2-methyldibenz[b,f]oxepin;

2-bromo-7-fluoro-11-[β-(dimethylamino)ethylthio]dibenz[b,f]oxepin;

10-[β-(ethylamino)ethylthio]-3-trifluoromethyldibenz[b,f]oxepin;

2-amino-10-[β-(ethylamino)ethylthio]dibenz[b,f]oxepin;

10-[β-(ethylamino)ethylthio]-3-methoxydibenz[b,f]oxepin;

10-[β-(diethylamino)ethylthio]-2-n-propyldibenz[b,f]oxepin;

10-[β-(methylamino)ethylthio]-3-methylthiodibenz[b,f]oxepin;

3-fluoro-11-[β-(methylamino)ethylthio]dibenz[b,f]oxepin;

3-ethyl-11-[β-(methylamino)ethylthio]dibenz[b,f]oxepin;

11-[β-(ethylamino)ethylthio]-4-nitrodibenz[b,f]oxepin; and 2-methyl-11-[β-(N-methyl-N-methoxycarbonyl)aminoethylthio]dibenz[b,f]oxepin.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in a form of their pharmaceutically acceptable addition salts for purposes of stability, convenience or crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampuls, disposable syringes or multiple dose vials made of glass or plastic.

The aminoalkylthiodibenzoxepins of the present invention are more stable to acid than the corresponding aminoalkoxydibenzoxepins as determined in the gas chromatographic assay described in Example 57.

EXAMPLE 1

A mixture of 1.6 g of 10,11-dihydro-10-hydroxydibenz[b,f]oxepin, 2.2 g of β-dimethylaminoethylthiol hydrochloride and 4 ml of boron trifluoride etherate in 8 ml of glacial acetic acid which was permitted to stand at ambient temperature for 64 hours is added dropwise to a stirring, cold 20% sodium hydroxide solution. The liberated amine is extracted into ether, washed successively with sodium hydroxide and a saturated sodium chloride solution and dried. The ether is removed under reduced pressure leaving a thick oil which is dissolved in acetone and converted to its crystalline oxalate. The salt is recrystallized from a methanol-acetone mixture leaving colorless crystals, mp 168°–169° C., of 10,11-dihydro-10-[β-(dimethylamino)ethylthio]dibenz[b,f]oxepin oxalate.

Analysis: Calculated for $C_{18}H_{21}NOS \cdot C_2H_2O_4$: 61.68%C; 5.95%H; 3.59%N; 8.23%S. Found: 61.50%C; 6.01%H; 3.54%N; 8.38%S.

EXAMPLE 2

A solution of 2.5 g of 10,11-dihydro-10-hydroxydibenz[b,f]oxepin, 4.01 g of β-diethylaminoethylthiol hydrochloride, 8 ml of boron trifluoride etherate in 13 ml of glacial acetic acid which was permitted to stand for 48 hours is concentrated and then poured into a cold 25% sodium hydroxide solution. The resulting oil is extracted into ether. The ether extracts are combined, and washed successively with dilute sodium hydroxide and water, and then dried. The dried solution is filtered and the filtrate evaporated to dryness leaving an oil. The oil is stirred with a 40% sodium hydroxide solution and then extracted into ether and dried. The ethereal solution is filtered, and the ether removed leaving another oil which is chromatographed through a silica gel column with a 20% methanol in chloroform eluant. The chromatographed product is converted to its oxalate, the white salt, mp 109°–111° C., of 10-[β-(diethylamino)ethylthio]-10,11-dihydrodibenz[b,f]oxepin oxalate.

Analysis: Calculated for $C_{20}H_{24}NOS \cdot C_2H_2O_4$: 63.44%C; 6.29%H; 3.36%N. Found: 63.54%C; 6.57%H; 3.23%N.

EXAMPLE 3

A solution of 0.55 g of 10,11-dihydro-10-[β-(dimethylamino)ethylthio]dibenz[b,f]oxepin, free base of Example 1, in 10 ml of chloroform is added dropwise to a solution of 0.28 g of cyanogen bromide and 0.6 g of potassium carbonate in 5 ml of chloroform. After total addition the reaction mixture is permitted to stand for 10 minutes and then filtered. The filtrate is concentrated to dryness leaving a thick oil which crystallizes upon standing. The crystalline mass is recrystallized from low boiling petroleum ether to give colorless needles, mp 77°–78° C., of 10-(β-bromoethylthio)-10,11-dihydrodibenz[b,f]oxepin.

Analysis: Calculated for $C_{16}H_{15}BrOS$: 57.32%C; 4.51%H; 23.84%Br. Found: 57.58%C; 4.57%H; 24.20%Br.

EXAMPLE 4

A mixture of 1.5 g of 10-(β-bromoethylthio)-10,11-dihydrodibenz[b,f]oxepin, Example 3, 0.5 g of N-methylpiperazine, 1.0 g of sodium bicarbonate, 1.0 g of potassium iodide in 15 ml of dimethylformamide is stirred at 80° C. for 16 hours. The mixture is permitted to cool before being diluted with water. The biphasic mixture is extracted thrice with 100 ml portions of ether. The ether extracts combined and shaken vigorously with a large excess of 2N hydrochloride acid. The acidic solution is basified to liberate the free amine. The amine is extracted into benzene, the benzene solution dried and the benzene removed under vacuum leaving a pale yellowish oil. The oil is dissolved in ether and converted to a crystalline dihydrobromide which is recrystallized from a methanol-acetone mixture to give white needles, mp 180°–182.5° C., of 10,11-dihydro-10-[β-(4-methylpiperazin-1-yl)ethylthio]dibenz[b,f]oxepin dihydrobromide.

Analysis: Calculated for $C_{21}H_{21}N_2OS.2HBr$: 48.84%C; 5.46%H; 5.42%N. Found: 48.93%C; 5.66%H; 5.29%N.

EXAMPLE 5

A mixture of 1.5 g of 10-(β-bromoethylthio)-10,11-dihydrodibenz[b,f]oxepin, Example 3, 0.5 g of morpholine, 1.0 g of sodium bicarbonate and 1.0 g of potassium iodide in 15 ml of dimethylformamide is stirred at 60°–70° C. for 64 hours. The reaction mixture is permitted to cool before being diluted with water. The biphasic mixture is extracted with ether and the combined ether extracts are shaken with a large excess of 2N hydrochloric acid. The acid solution is basified with potassium carbonate liberating the amine as an oil which is extracted into ether. The ethereal solution is dried and the ether is removed under vacuum regenerating an oil which is converted to its oxalate. The salt is recrystallized from a methanol-acetone-ether mixture to give colorless plates, mp 196°–198° C. of 10,11-dihydro-10-(β-morpholinoethylthio)dibenz[b,f]oxepin oxalate.

Analysis: Calculated for $C_{20}H_{23}NO_2S.C_2H_2O_4$: 61.23%C; 5.84%H; 3.26%N. Found: 60.77%C; 5.88%H; 3.20%N.

EXAMPLE 6

A sample of 3.8 g of 2-chloro-10,11-dihydro-11-hydroxydibenz[b,f]oxepin is treated with 3.3 g of β-dimethylaminoethylthiol hydrochloride in a manner consistent with the procedure of Example 1, to provide granular crystals, mp 139°–141° C. of 2-chloro-10,11-dihydro-11-[β-(dimethylamino)ethylthio]-dibenz[b,f]oxepin oxalate.

Analysis: Calculated for $C_{18}H_{28}ClNOS.C_2H_2O_4$: 56.66%C; 5.23%H; 3.31%N. Found: 56.58%C; 5.27%H; 3.31%N.

EXAMPLE 7

A solution of 2.0 g of 10,11-dihydro-10-oxodibenz[b,f]oxepin, 2.96 g of γ-dimethylaminopropylthiol hydrochloride and 8 ml of boron trifluoride etherate in 8 ml of glacial acetic acid which was permitted to stand for 16 hours is refluxed on a stream bath for 30 minutes, cooled and poured into a 6N sodium hydroxide solution. The reaction mixture is extracted with ether and the combined ether extracts are washed successively with a 25% sodium hydroxide solution and water and dried. The dried solution is filtered and the filtrate concentrated leaving an oil. The oil is chromatographed through a silica gel column with an eluant of 10% methanol in chloroform. The chromatographed oil is converted to its oxalic acid salt, mp 151°–152° C., which is 10-[γ-(dimethylamino)propylthio]dibenz[b,f]oxepin oxalate.

Analysis: Calculated for $C_{19}H_{21}NOS.C_2H_2O_4$: 62.82%C; 5.77%H; 3.49%N. Found: 62.71%C; 5.77%H; 3.43%N.

EXAMPLE 8

A mixture of 1.2 g of 10,11-dihydro-10-oxodibenz[b,f]oxepin, 2.4 g of β-dimethylaminoethylthiol hydrochloride and 2 ml of boron trifluoride etherate in 10 ml of glacial acetic acid which was stirred at ambient temperature for 16 hours is warmed on a steam bath for 30 minutes. The warm mixture is poured onto 200 g of ice-water and the diluted mixture basified with a 40% sodium hydroxide solution liberating an oil which is dissolved in ether. The ether solution is dried and concentrated leaving a thick oil which is converted in ether to a crystalline oxalic acid salt. The salt is recrystallized from a methanol-ether mixture to give granules, 147°–148° C. of 10-[β-(dimethylamino)ethylthio]-dibenz[b,f]oxepin oxalate.

Analysis: Calculated for $C_{18}H_{19}NOS.C_2H_2O_4$: 62.00%C; 5.46%H; 3.61%N; 8.28%S. Found: 61.88%C; 5.46%H; 3.55%N; 8.22%S.

EXAMPLE 9

To a stirring solution of 0.36 g of cyanogen bromide, 2.28 g of potassium carbonate in 10 ml of chloroform is added dropwise a solution of 1.0 g of 10-[β-(dimethylamino)ethylthio]dibenz[b,f]oxepin, Example 8, in chloroform. After total addition the reaction mixture is refluxed for 2 hours and the solvent removed leaving an oil. The oil is dissolved in 10 ml of methanol and the methanolic solution refluxed for 10 minutes and again concentrated to recover the oil. The oil is chromatographed through a silica gel column with an eluant of ether. The top fraction is collected and concentrated leaving a white solid, mp 106°–107° C. of 10-[β-(bromo)ethylthio]dibenz[b,f]oxepin.

Analysis: Calculated for $C_{16}H_{13}BrOS$: 57.66%C; 3.93%H; 9.62%S; 23.98%Br. Found: 58.38%C; 3.89%H; 9.84%S; 24.12%Br.

EXAMPLE 10

To a stirring solution of 0.36 g of cyanogen bromide, 2.28 g of potassium carbonate in 10 ml of chloroform is added dropwise a solution of 1.0 g of 10-[β-(dimethylamino)ethylthio]dibenz[b,f]oxepin, Example 8, in 20 ml of chloroform. After total addition the reaction mixture is treated according to Example 9. Following column chromatography the middle fraction is collected and concentrated leaving the white product, mp 54°–56° C., of 10-[β-(N-cyano-N-methylamino)ethylthio]dibenz[b,f]oxepin.

Analysis: Calculated for $C_{18}H_{16}N_2OS$: 70.10%C; 5.23%H. Found: 69.99%C; 5.28%H.

EXAMPLE 11

A solution of 2.0 g of 10,11-dihydro-10-oxodibenz[b,f]oxepin, 3.76 g of β-diisopropylaminoethylthiol hydrochloride, and 8 ml of boron trifluoride etherate in 10 ml of glacial acetic acid is treated according to Example 7 to produce a yellow oil. The oil is chromatographed through a silica gel column with an eluant of 5% methanol in chloroform. The chromatographed oil solidifies upon scratching to a pale yellow powder, mp 65°–66° C., of 10-[β-(diisopropylamino)ethylthio]dibenz[b,f]oxepin.

Analysis: Calculated for $C_{22}H_{27}NOS$: 74.74%C; 7.70%H; 3.96%N. Found: 74.95%C; 7.71%H; 4.06%N.

EXAMPLE 12

A mixture of 1.14 g of 10-[β-(bromo)ethylthio]dibenz[b,f]oxepin, Example 9, 0.36 g of morpholine, 0.92 g of sodium bicarbonate and 0.93 g of potassium iodide in 15 ml of dimethylformamide is stirred for 16 hours while maintaining the mixture between 60° and 65° C. Thereafter the mixture is poured into 150 ml of water, the biphasic mixture extracted with ether and the ether extracts combined and dried. The dried ether solution is filtered and the filtrate concentrated leaving an oil which is chromatographed through a silica gel column with an eluant of 5% methanol in chloroform. The chromatographed oil is converted to its white oxalic acid salt, mp 181°–183° C., of 10-[β-(morpholino)ethylthio]dibenz[b,f]oxepin oxalate.

Analysis: Calculated for $C_{20}H_{21}NO_2S.C_2H_2O_4$: 61.52%C; 5.40%H; 3.26%N. Found: 61.33%C; 5.35%H; 3.34%N.

EXAMPLE 13

To a stirred solution of 2.08 g of 10-[β-(dimethylamino)ethylthio]dibenz[b,f]oxepin, free base of Example 8, in 10 ml of methylene chloride is added dropwise a solution of 1.26 g of phenyl chloroformate in 10 ml of methylene chloride. After total addition the reaction mixture is permitted to stir at ambient temperature for 16 hours and then concentrated leaving an oily residue. The residue is triturated with hexane and then chilled at −20° C. to effect a solid. The solid is recrystallized from an ether-hexane mixture to give white needles, mp 103°–103.5° C., of 10-[β-(N-methyl-N-phenoxycarbonyl)aminoethylthio]dibenz[b,f]oxepin.

Analysis: Calculated for $C_{24}H_{21}NO_3S$: 71.42%C; 5.24%H; 3.47%N. Found: 71.37%C; 5.31%H; 3.51%N.

EXAMPLE 14

A stirring suspension of 1.6 g of 10-[β-(N-methyl-N-phenoxycarbonylamino)ethylthio]dibenz[b,f]oxepin, Example 13, and 3.4 g of potassium hydroxide pellets in 40 ml of ethylene glycol is heated to between 150° and 160° C. over a 60 minute span. Stirring is continued at this temperature for an additional 30 minutes. The mixture is cooled, diluted with water and the biphasic mixture extracted with an excess of ether. The ether extracts are combined, washed with water and dried and the solvent removed leaving a clear, mobile oil. The oil is converted to its oxalic acid salt and recrystallized from methanol to give shiny needles, mp 207°–208° C.(dec), of 10-[β(methylamino)ethylthio]dibenz[b,f]oxepin oxalate.

Analysis: Calculated for $C_{17}H_{17}NOS.C_2H_2O_4$: 61.11%C; 5.12%H; 3.75%N. Found: 60.85%C; 5.14%H; 3.78%N.

EXAMPLE 15

A mixture of 1.82 g of 10-[β-(methylamino)ethylthio]dibenz[b,f]oxepin, free base of Example 14, 0.72 g of cyclopropylmethyl chloride, 1.93 g of sodium bicarbonate and a few crystals of potassium iodide in 50 ml of dimethylformamide is stirred at 80° C. for 16 hours. The reaction mixture is permitted to cool and filtered and the filtrate concentrated leaving an oil which is converted to the oxalic acid salt, mp 137°–139° C., of 10-[β-(N-cyclopropylmethyl-N-methylamino)ethylthio]dibenz[b,f]oxepin oxalate.

Analysis: Calculated for $C_{21}H_{23}NOS.C_2H_2O_4$: 64.61%C; 5.89%H; 3.28%N. Found: 64.80%C; 5.96%H; 3.24%N.

EXAMPLE 16

A mixture of 1.5 g of 10-[β-(methylamino)ethylthio]dibenz[b,f]oxepin, free base of Example 14, 1.1 g of ethyl iodide, 1.48 g of sodium bicarbonate and 1.46 g of potassium iodide in 20 ml of dimethylformamide is stirred at 80°–85° C. for 16 hours. The reaction mixture is permitted to cool and diluted with 75 ml of water and then extracted thrice with 75 ml portions of ether. The ether extracts are combined, washed with 75 ml of a saturated sodium chloride solution and then dried. The dried solution is filtered and the filtrate concentrated leaving an oil. The oil is chromatographed through an alumina column with an eluant of ether. The chromatographed oil is converted to its oxalic acid salt which is recrystallized from an acetone-ether mixture to give the white product, mp 126°–128° C., of 10-[β-(N-ethyl-N-methylamino)ethylthio]dibenz[b,f]oxepin oxalate.

Analysis: Calculated for $C_{19}H_{21}NOS.C_2H_2O_4$: 62.82%C; 5.77%H; 3.49%N. Found: 62.39%C; 5.69%H; 3.56%N.

EXAMPLE 17

The substitution of propargyl bromide for ethyl iodide into the procedure of Example 16 provides the white solid, mp 140°–142° C., of 10-[β-(N-methyl-N-propargyl)aminoethylthio]dibenz[b,f]oxepin oxalate.

Analysis: Calculated for $C_{20}H_{19}NOS.C_2H_2O_4$: 64.21%C; 5.14%H; 3.40%N. Found: 64.49%C; 5.22%H; 3.41%N.

EXAMPLE 18

To a mixture at a temperature of 0° C. of 2.8 g of β-diethylaminoethylthiol hydrochloride in 5 ml of acetic acid and 5 ml of boron trifluoride etherate is added dropwise a solution of 2.0 g of 2-chloro-10,11-dihydro-11-hydroxydibenz[b,f]oxepin in 6 ml of glacial acetic acid. After total addition the reaction mixture at 0° C. is stirred for 20 minutes and thereafter at ambient temperature for 16 hours. The well stirred mixture is added slow to 50 ml of a 20% sodium hydroxide solution at 0° C. After this addition ether is added and the biphasic mixture filtered and permitted to form separate layers. The aqueous layer is extracted twice with 50 ml portions of ether and the ether extracts combined with the organic (ethereal) phase. The combined solutions are washed successively with one portion each of 40 ml of 20% sodium hydroxide solution, 30 ml of 10% sodium hydroxide, 50 ml of water and 30 ml of a saturated sodium chloride solution and then dried over potassium carbonate and potassium hydroxide pellets leaving an oil. The oil is chromatographed through a silica gel column with a 5% methanol chloroform mixture to obtain a purified oil which is dissolved in ether and treated with an ethereal oxalic acid solution to obtain the corresponding oxalic acid salt which is recrystallized from acetone to give a white powder, mp 126.5°–128.5° C., of 2-chloro-11-[β(diethylamino)ethylthio]-10,11-dihydrodibenz[b,f]oxepin oxalate.

Analysis: Calculated for $C_{20}H_{23}ClNOS.C_2H_2O_4$: 58.60%C; 5.59%H; 3.11%N; 7.86%Cl. Found: 58.68%C; 5.78%H; 2.95%N; 8.27%Cl.

EXAMPLE 19

To a stirred solution of 2.5 g of 10,11-dihydro-10-hydroxydibenz[b,f]oxepin, 3.7 g of γ-dimethylaminopropylthio hydrochloride in 13 ml of glacial acetic acid are added 8 ml of boron trifluoride etherate. The reaction mixture is permitted to stand for 24 hours before being poured into 50 ml of a chilled 25% sodium hydroxide solution. The basic mixture is extracted with ether, the ether extracts combined which are washed successively with a 20% sodium hydroxide solution and water, dried and filtered and the filtrate evaporated leaving an oil. The oil is chromatographed through a silica gel column with a 5% methanol in chloroform eluant and the eluate is evaporated leaving a purified oil which is converted to a white granular oxalic acid salt, mp 179°–181° C., of 10,11-dihydro-10-[γ-(dimethylamino)propylthio]dibenz[b,f]oxepin.

Analysis: Calculated for $C_{19}H_{22}NOS.C_2H_2O_4$: 62.66%C; 6.01%H; 3.48%N. Found: 62.60%C; 6.26%H; 3.64%N.

EXAMPLE 20

A mixture of 1.5 g of 10-[β-bromoethyl)thio]-10,11-dihydrodibenz[b,f]oxepin, Example 3, and 1.0 g of potassium iodide in 15 ml of dimethylformamide is bubbled for five minutes with ethylamine. The reaction mixture is permitted to cool to ambient temperature and then stirred for 16 hours. Ice-water is added and the biphasic mixture is extracted thrice with benzene and the combined benzene extracts are dried and evaporated to dryness leaving a crude product which is converted in acetone to its oxalic acid salt. The salt is recrystallized from 90% ethanol to give colorless prisms, mp 205°–207° C., dec, of 10-[β-(ethylamino)ethylthio]-10,11-dihydrodebenz[b,f]oxepin oxalate.

Analysis: Calculated for $C_{18}H_{21}NOS.C_2H_2O_4$: 61.67%C; 5.95%H; 3.60%N. Found: 61.68%C; 5.97%H; 3.39%N.

EXAMPLE 21

To a solution of 2.5 g of 10,11-dihydro-2-methylthio-11-oxodibenz[b,f]oxepin, 2.8 g of β-dimethylaminoethylthiol hydrochloride and 24 ml of glacial acetic acid which was stirred at ambient temperature for 30 minutes is added, with additional stirring, 8 ml of boron trifluoride etherate. After total addition, stirring is discontinued and the reaction mixture is permitted to stand for 72 hours before being added to 50 ml of ice-water. The diluted mixture is made strongly alkaline with a 10% sodium hydroxide solution and the strongly alkaline mixture is extracted with ether. The combined ether extracts are dried and evaporated to dryness leaving an oil. The oil is chromatographed through a silica gel column with a 5% methanol in chloroform eluant and the desired fractions were collected and concentrated leaving a purified oil. The oil was converted to a white granular oxalic acid salt of 11-[β-(dimethylamino)ethylthio]-2-methylthiodibenz[b,f]oxepin oxalate.

Analysis: Calculated for $C_{19}H_{21}NOS_2.C_2H_2O_4$: 58.18%C; 5.35%H; Found: 57.99%C; 5.26%H;

EXAMPLE 22

To a solution of 1.0 g of 2-fluoro-10,11-dihydro-11-oxodibenz[b,f]oxepin and 1.2 g of dimethylaminoethanthiol hydrochloride in 11 ml of glacial acetic acid is added 3.3 ml of boron trifluoride etherate. After total addition the reaction mixture is stirred at ambient temperature for 64 hours and them poured into 25 ml of solution at 0° C. of 20% sodium hydroxide and the aqueous mixture extracted with ether. The combined ether extracts are washed successively with two portions of 20% sodium hydroxide, one portion of water and one portion of a saturated sodium chloride solution and then dried to give an oil. The oil is chromatographed through a silica gel column with a 5% methanol in chloroform solution to give a purified oil which is treated with ethereal hydrogen bromide solution effecting a white precipitate. The precipitate is washed with ether and recrystallized from acetone to give a white powder, mp 197°–198.5° C. of 2-fluoro-11-[β-(dimethylamino)ethylthio]dibenz[b,f]oxepin hydrobromide.

Analysis: Calculated for $C_{18}H_{17}FNOS.HBr$: 54.55%C; 4.83%H; 3.54%N; 20.17%Br. Found: 54.49%C; 4.80%H; 3.50%N; 20.14%Br.

The 2-fluoro-10,11-dihydro-11-oxodibenz[b,f]oxepin, starting material for Example 22, can be prepared by the following sequence of reactions:

a. To 147 g of iodobenzoic acid and 45.5 g of potassium carbonate are added 57 ml of nitrobenzene. The mixture is heated with stirring at 160° C. for 40 minutes. To the heated mixture is added an additional 46.5 g of potassium carbonate and then successively 73.1 g of 4-fluorophenol, another 46.5 g of potassium carbonate and 0.3 g of copper powder. After these additions, the mixture is stirred at 160° C. for 45 minutes and the resulting solid is cooled to 0° C. The cooled solid is mixed with 100 ml of water and 220 ml of 6N hydrochloric acid. The acidic mixture is diluted with water to a volume of one liter and then mixed with 450 ml of chloroform. The white solid is filtered off and washed with chloroform and water. The solid is dissolved in hot acetone, cooled and filtered, to leave a white crystalline product, mp 146°–147° C. of 2-(4-fluorophenoxy)benzoic acid.

b. To 3.28 g of 2-(4-fluorophenoxy)benzoic acid is added 5.6 ml of 97% thionyl chloride. The reaction mixture is heated on a steam bath for 10 minutes and any excess thionyl chloride is then removed under reduced pressure. The residual liquid is dissolved in 30 ml of 1,2-dichloroethane and added dropwise over a 30 minute span to a mixture of 1.9 g of aluminum chloride in 5 ml of 1,2-dichloroethane. After total addition the reaction mixture is stirred at reflux for 2 hours and allowed to stand at ambient temperature for 64 hours. The mixture is poured onto a mixture of 150 ml of ice and water and 125 ml of ether. The biphasic mixture is filtered through paper and separated. The aqueous layer is collected and extracted twice with two portions (50 ml) of ether. The combined ether extracts are washed successively with two 25 ml portions of a saturated sodium bicarbonate solution and one 25 ml portion of saturated sodium chloride solution and then dried to give an oil. The oil is treated with hexane and the resulting solution decanted off and evaporated leaving a bright yellow crystalline solid. The solid is chromotographed through a silica-gel column with a chloroform eluant and is recrystallized from cyclohexane to give a yellow-white crystalline solid, mp 85.5°–87.5° C., of 2-fluoro-10,11-dihydro-11-oxodibenz[b,f]oxepin.

The ketones of which are starting materials of other examples may be prepared in a fashion similar to the procedure outlined above.

EXAMPLE 23

To a solution which was stirred at ambient temperature for 30 minutes, 2.5 g of 2-chloro-10,11-dihydro-11-oxodibenz[b,f]oxepin, 2.9 g of $\beta$-dimethylaminoethylthiol hydrochloride in 25 ml of glacial acetic acid is added with continuous stirring 5 ml of boron trifluoride etherate. After total addition the stirring is discontinued and the reaction mixture is permitted to stand for 24 hours. The reaction is basified with 10% sodium hydroxide solution and extracted with ether. The combined ether extracts are dried and filtered and then the solvent removed leaving an oil. The oil is chromatographed through a silica gel column with a 5% methanol in chloroform eluant to obtain a purified oil which is converted to a white oxalic acid salt, mp 183°–184° C. of 2-chloro-11-[$\beta$-(dimethylamino)ethylthio]dibenz[b,f]oxepin oxalate.

Analysis: Calculated for $C_{18}H_{18}ClNOS.C_2H_2O_4$: 56.93%C; 4.78%H. Found: 56.67%C; 4.70%H.

EXAMPLE 24

To a solution of 2.5 g of 10,11-dihydro-2-(methylthio)-11-oxodibenz[b,f]oxepin, 3.33 g of $\beta$-diethylaminoethylthiol hydrochloride and 24 ml of glacial acetic acid which was stirred for 30 minutes is added 8 ml of boron trifluoride etherate. After this addition the reaction mixture is permitted to stand for 72 hours before its addition to 50 ml of ice water. The diluted mixture is made strongly alkaline with a 10% sodium hydroxide solution and then extracted with ether. The combined ether extracts are dried, filtered and the ether evaporated off leaving a yellow oil. The oil is chromatographed through a silica gel in chloroform column with an eluant of 5% methanol in chloroform to purify the oil which is converted to its hydrogen bromide acid salt which is recrystallized from acetone to give the salt, mp 184°–186° C., of 11-[$\beta$-(dimethylamino)ethylthio]-2-(methylthio)dibenz[b,f]oxepin hydrobromide.

Analysis: Calculated for $C_{21}H_{25}NOS_2.HBr$: 55.74%C; 5.79%H; 3.10%N. Found: 55.83%C; 5.85%H; 3.05%N.

EXAMPLE 25

To a stirring solution of 11.3 g of 11-[$\beta$-(dimethylamino)ethylthio]-2-(methylthio)dibenz[b,f]oxepin, free base of Example 21, and 10.0 g of potassium carbonate in 50 ml of methylene chloride is added dropwise a solution of 5.7 g of phenylchloroformate in 50 ml of methylene chloride. After total addition the reaction mixture is stirred at ambient temperature for 24 hours and then evaporated to dryness. The residue is triturated with ether and the ethereal solution is sequentially washed successively with a 10% sodium hydroxide solution and water, dried and filtered and the filtrate evaporated to dryness leaving a yellow oil. The oil is chromatographed through a silica gel column with a methylene chloride eluant to obtain the purified orange oil of 11-[$\beta$-(N-methyl-N-phenoxycarbonylamino)ethylthio]-2-(methylthio)-dibenz[b,f]oxepin.

Analysis: Calculated for $C_{25}H_{23}NO_3S_2$: 66.79%C; 5.16%H; 3.12%N. Found: 66.84%C; 4.93%H; 3.06%N.

EXAMPLE 26

A mixture of 8.3 g of 11-[$\beta$-(N-methyl-N-phenoxycarbonyl)aminoethylthio]-2-(methylthio)-dibenz[b,f]oxepin, Example 25, 190 ml of ethylene glycol and 16 g of potassium hydroxide is stirred at 155° C. for 30 minutes. The reaction mixture is cooled and then poured onto 500 ml of ice water. The biphasic mixture is extracted with a 1:1 ether benzene mixture and the combined extracts are washed with water and dried. The dried solution is filtered and the filtrate evaporated to dryness leaving an oil. The oil is converted to its maleic acid salt which is recrystallized from acetone leaving the salt, mp 160°–162° C. of 11-[$\beta$-(methylamino)ethylthio]-2-(methylthio)dibenz[b,f]oxepin maleate.

Analysis: Calculated for $C_{18}H_{19}NOS_2.C_4H_4O_4$: 59.30%C; 5.20%H; 3.14%N. Found: 59.40%C; 5.23%H; 3.08%N.

EXAMPLE 27

A reaction solution of 1.9 g of 11-[$\beta$-(methylamino)ethylthio]-2-(methylthio)dibenz[b,f]oxepin, free base of Example 26, 1.2 g of ethyl iodide and 1.60 g of sodium bicarbonate in 25 ml of dimethylformamide is stirred with heating for 72 hours. The solution is diluted with 100 ml of water and the biphasic mixture extracted with ether. The combined ether extracts are washed with water, dried and then filtered and the filtrate evaporated to dryness leaving an oil. The oil is converted to a white salt, mp 112°–114° C. of 11-[$\beta$-ethylmethylamino)ethylthio]-2-(methylthio)dibenz[b,f]oxepin maleate.

Analysis: Calculated for $C_{20}H_{23}NOS_2.C_4H_4O_4$: 60.86% C; 5.75% H; 2.96% N. Found: 61.11% C; 5.74% H; 2.87% N.

EXAMPLES 28 AND 29

By following the procedure of Example 25, 2-fluoro-11-[$\beta$-(dimethylamino)ethylthio]dibenz[b,f]oxepin, free base of Example 22, and 2-chloro-10,11-dihydro-11-[$\beta$-(dimethylamino)ethylthio]dibenz[b,f]oxepin, free based of Example 6, are treated respectively to obtain 2-fluoro-11-[$\beta$-(N-methyl-N-phenoxycarbonylamino)ethylthio]dibenz[b,f]oxepin, Example 28, and 2-chloro-11-[$\beta$-(N-methyl-N-phenoxycarbonylamino)ethylthio]-dibenz[b,f]oxepin, Example 29.

Analysis: [Example 28]Calculated for $C_{24}H_{20}FNO_3S$: 68.40% C; 4.78% H; 3.32% N; 4.51% F. Found: 68.25% C; 4.85% H; 3.28% N; 4.80% F.

EXAMPLE 30

A reaction solution of 5.1 g of 2-fluoro-11-[$\beta$-(N-methyl-N-phenoxycarbonylamino)ethylthio]dibenz[b,f]oxepin and 10.6 g of potassium hydroxide in 125 ml of ethylene glycol is stirred with heating at from 80° to 155° C. for 30 minutes and then at 155° C. for 30 minutes. Then the reaction is permitted to stand at 0° C. for 16 hours before being poured onto 350 ml of ice water. The biphasic mixture is extracted thrice with 125 ml portions of 1:1 ether-benzene mixture. The combined organic layers are washed successively with three portions of water and one portion of a saturated sodium chloride solution and then dried leaving a clear orange oil. The oil is swirled with a 50 ml portion and 0.25 ml portion of boiling hexane and decanted from any residue effecting a yellow oil. The oil is treated in ether with ethereal maleic acid effecting a salt which is recrystallized from a methanol-acetone-ether mixture to give a white powder, mp 135.5°–136° C., of 2-fluoro-11-[β-(methylamino)ethylthio]dibenz[b,f]oxepin maleate.

Analysis: Calculated for $C_{17}H_{16}FNOS.C_4H_4O_4$: 60.43% C; 4.83% H; 3.36% N; 4.55% F. Found: 60.42% C; 4.86% H; 3.26% N; 4.85% F.

EXAMPLE 31

A reaction mixture of 4.0 g of 2-chloro-11-[β-(N-methyl-N-phenoxycarbonylamino)ethylthio]dibenz[b,f]oxepin, Example 29, and 8.5 g of potassium hydroxide in 80 ml of ethylene glycol is stirred at 155° C. for 30 minutes. The mixture is permitted to cool and ice is added. The mixture is extracted with ether and the combined ether extracts are dried and the ether evaporated off leaving an oil. The oil is treated in ether with ethereal maleic acid and the resulting salt recrystallized from a methanol-ether mixture to give colorless prisms, mp 153°–154° C., of 2-chloro-11-[β-(methylamino)ethylthio]dibenz[b,f]oxepin maleate.

Analysis: Calculated for $C_{17}H_{16}ClNOS.C_4H_4O_4$: 58.12% C; 4.64% H; 3.22% N; 8.17% Cl. Found: 58.15% C; 4.77% H; 3.24% N; 8.33% Cl.

EXAMPLE 32

To a mixture of 1.1 g of β-dimethylaminoethanethiol hydrochloride and 2.8 ml of boron trifluoride ethereate in 5 ml of glacial acetic acid is added dropwise a solution of 0.9 g of 2-fluoro-10,11-dihydro-11-hydroxydibenz[b,f]oxepin in 4.4 ml of glacial acetic acid. After total addition the reaction mixture is permitted to stir for 16 hours before being poured onto a mixture of 30 ml of a 20% sodium hydroxide solution and ice. The mixture is extracted with ether and the combined ether extracts are washed successively with two-portions of a 20% sodium hydroxide solution, one portion of water and one portion of a saturated sodium chloride solution. The washed extracts are dried producing an oil which is chromatographed through a silica gel column with an eluant of 5% methanol in chloroform to obtain a purified oil. The oil is converted to its oxalic acid salt which is recrystallized from acetone to give a white powder, mp 169°–170.5° C., of 2-fluoro-10,11-dihydro-11-[β-(dimethylamino)ethylthio]dibenz[b,f]oxepin oxalate.

Analysis: Calculated for $C_{18}H_{20}FNOS.C_2H_2O_4$: 58.96% C; 5.44% H; 3.44% N; 4.66% F. Found: 59.17% C; 5.44% H; 3.51% N; 4.81% F.

EXAMPLE 33

To a mixture of 2.3 g of cyanogen bromide and 5.0 g of potassium carbonate in 40 ml of chloroform is added portion-wise over a 50 minutes span a solution of 4.8 of 2-fluoro-10,11-dihydro-11-[β-(dimethylamino)ethylthio]dibenz[b,f]oxepin, free base of Example 32, in 85 ml of chloroform. After total addition, the mixture is stirred for 20 minutes before being filtered. The filtrate is evaporated to leave an oil which is treated with three portions of boiling hexane. The combined hexane portions are evaporated leaving an oil which is chromatographed through a silica gel column with an eluant of methylene chloride and is recrystallized from cold hexane to give a white powder, mp 46°–48° C. of 11-[β-(bromo)ethylthio]-2-fluoro-10,11-dihydrodibenz[b,f]oxepin.

Analysis: Calculated for $C_{16}H_{14}BrFOS$: 54.41% C; 4.00% H; 22.63% Br; 5.38% F. Found: 54.36% C; 4.01% H; 22.91% Br; 5.69% F.

EXAMPLE 34

Methylamine is bubbled into 10 ml of dimethylsulfoxide for 5 minutes. To this solution is added dropwise a solution of 2.2 g of 11-[β-(bromoethyl)thio]-2-fluoro-10,11-dihydrodibenz[b,f]oxepin in 11 ml of dimethylsulfoxide. Sufficient methylamine is bubbled into the reaction mixture to complete the reaction. Thereafter the reaction mixture is permitted to stand for 64 hours. The reaction mixture is poured onto 125 ml of ice water, and the biphasic mixture is extracted with three portions of ether. The combined ether extracts are washed successively with two 40 ml portions of water and one 10 ml portion of saturated sodium chloride solution and dried to produce an oil. The oil is dissolved in ether and treated with ethereal maleic acid which precipitates a salt which is recrystallized from an acetone-ether mixture to give a white solid, mp 118°–119.5° C., of 2-fluoro-10,11-dihydro-11-[β-(methylamino)ethylthio]dibenz[b,f]oxepin maleate.

Analysis: Calculated for $C_{17}H_{18}FNOS.C_4H_4O_4$: 60.14% C; 5.29% H; 3.34% N; 4.53% F. Found: 60.11% C; 5.19% H; 3.19% N; 4.80% F.

EXAMPLE 35

To a stirring solution of 2.8 g of β-dimethylaminoethylthiol hydrochloride and 7 ml of boron trifluorine etherate in 10 ml of glacial acetic acid is added dropwise a solution of 2.5 g of 10,11-dihydro-11-hydroxy-2-methylthiodibenz[b,f]oxepin in 10 ml of glacial acetic acid. After total addition the reaction mixture was permitted to stand for 24 hours before being added to 50 ml of a cold 25% sodium hydroxide solution. The reaction mixture is extracted with ether and the combined ether extracts are successively washed with a 20% sodium hydroxide solution and water and dried. The dried solution is filtered and the filtrate is evaporated to dryness leaving an oil which is dissolved in chloroform. The chloroform solution is chromatographed through a silica gel column with an eluant of 5% methanol in chloroform to obtain a purified oil. The purified product is converted to its maleic acid salt, a white powder, mp 100°–102° C. of 10,11-dihydro-11-[β-(dimethylamino)ethylthio]-2-(methylthio)dibenz[b,f]oxepin maleate.

Analysis: Calculated for $C_{19}H_{23}NOS_2.C_4H_4O_4$: 59.84% C; 5.90% H; 3.04% N. Found: 59.92% C; 5.93% H; 3.00% N.

EXAMPLE 36

By the procedure of Example 35, β-diethylaminoethylthiol hydrochloride is treated with 10,11-dihydro-11-hydroxy-2-methylthiodibenz[b,f]oxepin to obtain an oil of 11-[β-diethylamino)ethylthio]-10,11-dihydro-2-(methylthio)dibenz[b,f]oxepin. The oil is chromatographed through a silica gel-methylene chloride column with an eluant of a 5% methanol in methylene chloride to purify the oil. The purified oil is converted to its white oxalate salt, mp 118°–120° C.

Analysis: Calculated for $C_{21}H_{27}NOS_2.C_2H_2O_4$: 59.58% C; 6.31% H; 3.02% N. Found: 59.30% C; 6.32% H; 2.93% N.

EXAMPLE 37

A sample of 10,11-dihydro-11-[β-(dimethylamino)ethylthio]-2-(methylthio)dibenz[b,f]oxepin, free base of Example 35, is treated according to the procedure of Example 33, to obtain 11-(β-bromoethylthio)-10,11-dihydro-2-(methylthio)dibenz[b,f]oxepin. The oil is dissolved in hexane and cooled in a dry/acetone bath to effect crystallization of the oil to a white solid, mp 64°–66° C.

Analysis: Calculated for $C_{17}H_{17}BrOS_2$: 53.54% C; 4.49% H; 20.96% Br. Found: 53.72% C; 4.47% H; 21.04% Br.

EXAMPLE 38

To a mixture of 2.0 g of 2-fluoro-11-[β-dimethylamino)ethylthio]dibenz[b,f]oxepin, free base of Example 22, 62 ml of methanol are added 6.1 g of magnesium shavings. The reaction is stirred for 90 minutes with sufficient cooling to maintain the reaction at ambient temperature. The methanolic mixture is decanted off and then cooled. The cooled mixture is then treated with careful addition of 60 ml of 6N hydrochloric acid. The acidified mixture is permitted to reach ambient temperature before being diluted with 60 ml of water and the diluted mixture is extracted with chloroform. The combined chloroform extracts are successively washed with 80 ml of a 10% sodium hydroxide solution, 100 ml of water and 25 ml of saturated sodium chloride solution and dried to effect a yellow oil. The oil is extracted thrice with 30 ml portions of hot pentane and the combined pentane extracts are evaporated leaving purer oil which is treated in ether with ethereal oxalic acid to precipitate out a salt. The salt is washed well with ether leaving a white solid, mp 167°–169° C. of 2-fluoro-10,11-dihydro-11-[β-(dimethylamino)ethylthio]dibenz[b,f]oxepin oxalate identical to the product described in Example 32.

By applying the aforesaid procedure, 10-[β-(dimethylamino)ethylthio]dibenz[b,f]oxepin, the free base of the compound of Example 9, is reduced to 10,11-dihydro-10-[β-(dimethylamino)ethylthio]dibenz[b,f]oxepin, the oxalate of which is identical to the compound of Example 1, 2-chloro-11-[β-(dimethylamino)ethylthio]dibenz[b,f]oxepin, the free base of the compound of Example 23, is reduced to 2-chloro-10,11-dihydro-11-[(β-dimethylamino)ethylthio]dibenz[b,f]oxepin, the oxalate of which is identical to the compound of Example 6, 2-fluoro-11-[β-(dimethylamino)ethylthio]dibenz[b,f]oxepin, the free base of the compound of Example 22, is reduced to 2-fluoro-10,11-dihydro-11-[β-(dimethylamino)ethylthio]dibenz[b,f]oxepin, the oxalate of which is identical to the compound of Example 23 and 2-fluoro-11-[β-(methylamino)ethylthio]dibenz[b,f]oxepin, the free base of the compound of Example 30, is reduced to 2-fluoro-10,11-dihydro-11-[β-(methylamino)ethylthio]dibenz[b,f]oxepin, the maleate of which is identical to the compound of Example 34.

EXAMPLE 39

A solution of 1.5 g of 11-[β-(bromo)ethylthio]-10,11-dihydro-2-(methylthio)dibenz[b,f]oxepin, Example 37, and 0.9 g of potassium iodide in 15 ml of dimethylformamide is stirred at ambient temperature while methylamine is bubbled into the solution over a 5 minute span. After total addition, the solution is permitted to stir for 16 hours before being successively poured into 100 ml of ice water, extracted with benzene, and the combined benzene extracts dried. The dried solution is filtered and then evaporated to dryness leaving a yellow oil which is converted to its maleic acid salt as a granular powder which is recrystallized from a methanol-ether mixture to provide the product, mp 138°–140° C., of 10,11-dihydro-11-[β-(methylamino)ethylthio]-2-methylthiodibenz[b,f]oxepin maleate.

Analysis: Calculated for $C_{18}H_{21}NOS_2 \cdot C_4H_4O_4$: 59.04% C; 5.63% H; 3.13% N. Found: 58.83% C; 5.43% H; 2.90% N.

EXAMPLE 40

Into a solution of 2.6 g of 10-(β-bromoethylthio)-10,11-dihydrodibenz[b,f]oxepin, Example 3, in 15 ml of dimethylformamide is bubbled methylamine over a 20 minute span. After total addition the reaction mixture is permitted to stand at ambient temperature for 16 hours. Thereafter, ice water is added and the biphasic mixture is extracted thrice with ether and the combined ether extracts are washed with water. The ethereal solution is dried and the resulting product is converted to its maleic acid salt. The salt is recrystallized from an acetone-ether mixture to provide prisms, mp 102°–104° C. of 10,11-dihydro-10-[(β-methylamino)ethylthio]dibenz[b,f]oxepin maleate.

Analysis: Calculated for $C_{17}H_{19}NOS \cdot C_4H_4O_4$: 62.82% C; 5.77% H; 3.49% N; 7.99% S. Found: 62.80% C; 5.77% H; 3.36% N; 8.18% S.

EXAMPLE 41

A mixture of 2-chloro-10,11-dihydro-11-[β-(dimethylamino)ethylthio]dibenz[b,f]oxepin, free base of Example 6, 0.7 g of cyanogen bromide, and 0.8 g of potassium carbonate in 20 ml of methylene chloride is stirred at ambient temperature for 4 hours. Thereafter the mixture is filtered and the filtrate concentrated under vacuum, leaving a viscous oil. The oil is chromatographed over silica gel, leaving a pale yellowish oil, Rf of 0.8, of 11-(β-bromoethylthio)-2-chloro-10,11-dihydrodibenz[b,f]oxepin.

Analysis: Calculated for $C_{16}H_{14}BrClOS$: 51.98% C; 3.82% H; 8.67% S. Found: 52.26% C; 3.76% H; 8.61% S.

EXAMPLE 42

Into a solution of 1.5 g of 11-[β-(bromo)ethylthio]-2-chloro-10,11-dihydrodibenz[b,f]oxepin, Example 41, in 20 ml of dimethylformamide is bubbled methylamine over a 10 minute span. Thereafter, the solution is permitted to stand at ambient temperature for 16 hours. Then the solution is evaporated to dryness leaving a yellowish oily residue which is equilibrated with sodium bicarbonate and ether. The ethereal phase is collected and then dried before being concentrated under vacuum leaving a clear oil which is converted to a crystalline maleic acid salt. The salt is recrystallized from an acetone-ether mixture to provide white prisms, mp 138°–140° C. of 2-chloro-10,11-dihydro-11-[β-(methylamino)ethylthio]dibenz[b,f]oxepin maleate.

Analysis: Calculated for $C_{17}H_{18}ClNOS \cdot C_4H_4O_4$: 57.86% C; 5.09% H; 3.21% N; 8.13% C. Found: 57.62% C; 5.00% H; 3.05% N; 8.33% C.

EXAMPLE 43 a. A solution of 28.4 g of 2-(4-methylsulfonylphenoxy)benzyl nitrile, 99 ml of 95% ethanol, 15.2 g of 85% potassium hydroxide and 25 ml of water is stirred at 115° C. for 24 hours. Thereafter, the reaction mixture is concentrated to an oil. The oil is dissolved in water and the aqueous solution is washed with ether, acidified with dilute hydrochloric acid providing an oil. This oil is dissolved in methylene chloride and the solution, successively, is dried, filtered and concentrated to dryness leaving a light yellow solid. The solid is chromatographed through a silica gel/ether column with a 10% methanol in ether eluant to provide the product 2-(4-methylsulfonylphenoxy)phenylacetic acid, mp 125°–127° C.

b. A mixture of 1.0 g of 2-(4-methylsulfonylphenoxy)-phenylacetic acid and 10 ml of polyphosphoric acid under nitrogen is stirred at 90°–100° C. for 2 hours. The reaction mixture is permitted to cool and then poured into 100 ml of an ice-water slurry. The aqueous solution is basified with 20% sodium hydroxide before being extracted with methylene chloride. The combined extracts are dried and then evaporated to dryness leaving an oil. The oil is chromatographed through a silica gel/methylene chloride column with 2% methanol in methylene chloride. The chromatographed solution is evaporated to dryness leaving an oil which solidifies on standing. The solid is triturated with pentane to provide 10,11-dihydro-2-methylsulfonyl-11-oxodibenz[b,f]oxepin, mp 105°–106° C.

c. A stirring solution of 4.4 g of 10,11-dihydro-2-methylsulfonyl-11-oxodibenz[b,f]oxepin, 4.3 g of dimethylaminoethylthiol hydrochloride and 37 ml of glacial acetic acid is treated with 15 ml of boron trifluoride etherate. Thereafter the reaction mixture is poured into 300 ml of a cold 10% sodium hydroxide solution and the resulting solution is extracted with methylene chloride. The combined extracts are washed with water and dried before being filtered. The filtrate is evaporated to dryness leaving an oil which is chromatographed through silica gel/methylene chloride with a 2–4% methanol chloride eluant. The chromatographed solution is evaporated to dryness and the resulting oil is converted to a white maleic acid salt, mp 137°–139° C. of 11-[($\beta$-dimethylamino)ethylthio]-2-methylsulfonyl-dibenz[b,f]oxepin maleate.

Analysis: Calculated for $C_{19}H_{21}NO_3S_2 \cdot C_4H_4O_4$: 56.19% C; 5.13% H; 2.85% N. Found: 56.24% C; 5.15% H; 2.86% N.

EXAMPLE 44

To a solution of 3.5 g of 10,11-dihydro-10-oxodibenz[b,f]oxepin and 41.5 ml of acetic acid is added 6.04 g of $\beta$-(2-phenylethylamino)ethanethiol followed by 13 ml of boron trifluoride etherate. The reaction is stirred at ambient temperature for 24 hours, at 70°–80° C. for 90 minutes and allowed to cool to ambient temperature. The reaction is then poured into 100 ml of 20% sodium hydroxide solution containing 75 ml of ice and the pH is adjusted to a value of 9 by the addition of 10 ml of 50% sodium hydroxide solution. The mixture is shaken with 150 ml of ether and the layers are passed through a filter and separated. The combined ether extracts are washed successively with three 50 ml portions of 25% sodium hydroxide solution, three 50 ml portions of water and one 25 ml portion of saturated sodium chloride solution, dried over anhydrous magnesium sulfate, filtered and evaporated to give 7.30 g of an oil. The oil is chromatographed on a 4.5×20 cm column of silica gel (190 g) eluted with 5% methanol-dichloromethane to give 4.87 g of an oily residue after evaporation of the eluant. The residue is dissolved in ether and treated with an ethereal solution of maleic acid. Recrystallization of the precipitate from methanol-acetone-ether affords white crystals, mp 164°–164.5° C., of 10-[$\beta$-(2-phenylethylamino)ethylthio]dibenz[b,f]oxepin maleate.

Analysis: Calculated for $C_{24}H_{25}NOS \cdot C_4H_4O$: 68.70% C; 5.56% H; 2.86% N. Found: 68.78% C; 5.57% H; 2.52% N.

EXAMPLE 45

To a solution of 1.79 g of 10-[$\beta$-(2-phenylethylamino)ethylthio]dibenz[b,f]oxepin, the free base of Example 44, and 47 ml of dry methanol cooled in an ice-bath to 7° C. is added 4.61 g of magnesium shavings. The reaction is stirred at 7°–10° C. for 3 minutes. The ice-bath is removed and the reaction is stirred at ambient temperature for an additional 90 minutes. The solids are removed by decantation. The solution is cooled and 50 ml of 6N hydrochloric acid is slowly added. The mixture is diluted with 50 ml of water and extracted with three 50 ml portions of chloroform. The combined organic extracts are washed with 100 ml of 5% sodium hydroxide solution, two 75 ml portions of water and 20 ml of saturated sodium chloride solution, dried over anhydrous magnesium sulfate and filtered to afford 1.98 g of an oil. The oil is chromatographed on a 2.5×40 cm column of silica gel (40 g) eluted with 5% methanol-dichloromethane to give 1.55 g of an oily residue after evaporation of the eluant. The residue is dissolved in ether and treated with an ethereal solution of maleic acid. Recrystallization of the precipitate from acetone-ether affords white crystals, mp 125°–126° C., of 10,11-dihydro-10-[$\beta$-(2-phenylethylamino)ethylthio]-dibenz[b,f]oxepin maleate.

Analysis: Calculated for $C_{24}H_{25}NOS \cdot C_4H_4O_4$: 68.42% C; 5.95% H; 2.85% N. Found: 68.78% C; 5.92% H; 2.55% N.

EXAMPLE 46

To a solution of 1 g of trans-stilbene and 55.5 ml of dry methanol is added 1.35 g of magnesium shavings. The reaction is stirred at ambient temperature for 90 minutes and the solids are removed by decantation. The solution is cooled in an ice-bath and 180 ml of 1N hydrochloric acid is added. The mixture is extracted with chloroform. The combined organic extracts are washed with water, saturated sodium chloride solution, dried over anhydrous magnesium sulfate and filtered to afford 1.04 g of crystalline product, mp 48°–52° C., identical with an authentic sample, obtained from Aldrich Chemical Company, Milwaukee, Wis., by nuclear magnetic resonance, infrared and mass spectral analysis.

By employing the aforesaid procedure, 1.00 g of cis-stilbene is reduced to 1.02 g of crystalline product, mp 51°–52.5° C., identical to an authentic sample by the aforementioned analysis.

Styrene may be reduced to ethylbenzene by the above reduction method.

EXAMPLE 47

To a solution of 1.00 g of 1,1-diphenylethylene and 55.5 ml of dry methanol heated to 50° C. in an oil bath is added 1.35 g of magnesium shavings. The reaction is stirred at 50° C. for 90 minutes and worked up according to the procedure described in Example 46 to give an oil, the spectral properties (mass, infrared and nuclear magnetic resonance) of which are identical to those of an authentic sample of 1,1-diphenylethane.

EXAMPLE 48

To a solution of 1.00 g of 5H-dibenz[b,f]azepin and 52 ml of dry methanol is added 1.26 g of magnesium shavings in one portion. The reaction is stirred at ambient temperature for 90 minutes and worked up according to the procedure described in Example 46 to give a crystalline solid, the melting behavior and spectral properties (mass, infrared and nuclear magnetic resonance) of which one identical to those of authentic 5H-dibenz-10,11-dihydro[b,f]azepin.

EXAMPLE 49

To a boiling solution of 1.00 g of phenanthrene and 56 ml of dry methanol is added 2.72 g of magnesium shavings in one portion. The reaction is heated under reflux for 90 minutes and worked up according to the procedure described in Example 46 to give an amorphous solid, the proton magnetic resonance spectrum and vapor phase chromatographed (2 mm, inside diameter, ×6 ft silinized column of 3% OV-17 on 60/80 Gas Chrom Q at 160° C.) of which indicated it to be about a 50/50 mixture of 9,10-dihydrophenanthrene and unreacted starting material.

EXAMPLE 50

To a solution of 503 mg of 1-methyl-4-(5-dibenzo[a,e]cycloheptatrienylidene)piperidine, obtained by basification of its hydrochloride, and 17.5 ml of dry methanol heated to 50° C. in an oil bath is added 426 mg of magnesium shavings. The reaction is stirred at 50° C. for 3 hours. 6N Hydrochloric acid (10 ml) and water (55 ml) are added to the reaction and the mixture is extracted with chloroform. The combined organic extracts are washed successively with 10% sodium hydroxide solution, water, saturated sodium chloride solution, dried over anhydrous magnesium sulfate and filtered and evaporated to afford 1-methyl-4-(5-dibenzo-10,11-dihydro[a,e]cycloheptatrienylidene)piperidine as an oil which crystallized on standing.

EXAMPLE 51

To a mixture of 2.26 g of allylamine, 0.25 g of potassium iodide, 1.5 g of sodium bicarbonate and 10 ml of dimethylsulfoxide (sieve dried) is added a solution of 3.50 g of 11-[β-(bromoethyl)thio]-2-fluoro-10,11-dihydrodibenz[b,f]oxepin in 15 ml of dimethylsulfoxide (sieve dried) over 1 minute. The reaction mixture is stirred for 3 hours at room temperature and then poured into 250 ml of ice water. The mixture is extracted with three 150 ml portions of ether. The ethereal extracts are washed with three 10 ml portions of water, one 15 ml portion of saturated sodium chloride solution, dried over anhydrous magnesium sulfate and filtered. The filtrate is treated with a solution of maleic acid in ether to form a salt, the recrystallization of which from acetone-ether gives a white crystalline powder, mp 100°–102° C., of 11-[β-(alkylamino)ethylthio]-2-fluoro-10,11-dihydrodibenz[b,f]oxepin maleate.

Analysis: Calculated for $C_{19}H_2.FNOS.C_4H_4O_4$: 62.01% C; 5.42% H; 3.15% N; 4.27% F. Found: 61.94% C; 5.17% H; 2.82% N; 4.21% F.

EXAMPLE 52

A mixture of 2.43 g of 4-(4-fluorobenzoyl)piperidine hydrochloride, 3.0 g of sodium bicarbonate and 15 ml of anhydrous dimethylformamide is stirred for 30 minutes and cooled. To the mixture is added 2.6 g of 10-[β-(bromoethyl)thio]-10,11-dihydrodibenz[b,f]oxepin in 10 ml of anhydrous dimethylformamide, with stirring. The reaction mixture is stirred at 65°–70° C. for 16 hours and poured into ice water. The mixture is extracted with ether and the ether extracts are dried over anhydrous magnesium sulfate, filtered and evaporated. The residual oil was dissolved in ether and passed through a column of alumina. Evaporation of the eluant and treatment of the oily residue with ethereal hydrogen chloride affords a salt, the recrystallization of which from ethanol-ether gives crystals, mp 176°–178° C., of 10-[β-[4-(4-fluorobenzoyl)-1-piperidinyl]ethylthio]-10,11-dihydrodibenz[b,f]oxepin hydrochloride.

Analysis: Calculated for $C_{28}H_{28}FNOS.HCl$: 67.52% C; 5.87% H; 2.81% N; 3.81% F. Found: 67.32% C; 5.91% H; 2.58% N; 3.82% F.

EXAMPLE 53

To a mixture of 4.53 g of β-phenethylamine, 0.25 g of potassium iodide, 1.5 g of sodium bicarbonate in 9 ml of sieve dried dimethylsulfoxide, under nitrogen, is added a solution of 3.30 g of 11-[β-(bromoethyl)thio]-2-fluoro-10,11-dihydrodibenz[b,f]oxepin in 14.5 ml of dry dimethylsulfoxide over 50 seconds. The reaction is stirred at room temperature for 5 hours, poured into 250 ml of ice water and extracted with three 150 ml portions of ether. The combined ether extracts are washed with five 100 ml portions of water, one 20 ml portion of saturated sodium chloride solution, dried over anhydrous magnesium sulfate and filtered to give 4.66 g of an oil. The oil is chromatographed on a 3.5×25 cm (95 g) column of silica gel with 5% methanol-dichloromethane to give 3.03 g of an oil. The oil, in ether, is treated with ethereal maleic acid. The precipitated salt is washed with ether and recrystallized from acetone-ether to give a white crystalline powder, mp 129°–131° C., of 2-fluoro-10,11-dihydro-11-[β-(2-phenylethylamino)ethylthio]dibenz[b,f]oxepin maleate.

Analysis: Calculated for $C_{24}H_{24}FNOS.C_4H_4O_4$: 66.00% C; 5.54% H; 2.75% N; 3.73% F. Found: 65.99% C; 5.54% H; 2.50% N; 3.92% F.

EXAMPLE 54

To a mixture of 3.66 g of cyclopropylmethylamine hydrochloride, 0.25 g of potassium iodide and 1.5 g of sodium bicarbonate is added 10 ml of sieve dried dimethylsulfoxide. The mixture is stirred for one hour at room temperature, for 30 minutes at 55° C. and then cooled to room temperature. A solution of 3.00 g of 11-[β-(bromoethyl)thio]-2-fluoro-10,11-dihydrodibenz[b,f]oxepin in 100 ml of dry dimethylsulfoxide is added over 60 seconds and the reaction is stirred for one hour. Three additional grams of sodium bicarbonate is added and the reaction is stirred in an oil bath for 17 hours at 55°–60° C. and 4.5 hours at 75°–80° C. The reaction mixture is poured into 250 ml of ice water and three 150 ml ether extractions are performed. The ethereal solution is evaporated at 60° C. to remove excess amine and the residue is diluted with 250 ml of ether. The ethereal solution is washed with four 100 ml portions of water, one 25 ml portion of saturated sodium chloride solution, dried over anhydrous magnesium sulate and filtered to give 2.82 g of an oil. The oil is dissolved in ether and treated with ethereal maleic acid. The resulting salt is washed with ether and recrystallized thrice from acetone-ether to give a white powder, mp 124°–125° C., of 11-[β-(cyclopropylmethylamino)e- thylthio]-2-fluoro-10,11-dihydrodibenz[b,f]oxepin maleate.

Analysis: Calculated for $C_{20}H_{22}FNOS \cdot C_4H_4O_4$: 62.74% C; 5.70% H; 3.05% N; 4.13% F. Found: 62.88% C; 5.39% H; 3.20% N; 4.27% F.

EXAMPLE 55

Central Nervous System Depressant (Neuroleptic) Activity Climbing Mice Assay

METHOD:

The subject CD-1 male mice (23–27 grams) were group-housed under standard laboratory conditions. The mice were individually placed in wire mesh stick cages (4"×4"×10") and were allowed one hour for adaptation and exploration of the new environment. Then apomorphine was injected subcutaneously at 1.5 mg/kg, a dose causing climbing in all subjects for 30 minutes. Compounds to be tested for neuroleptic activity were injected intraperitoneally 30 minutes prior to the apomorphine challenge at a screening dose of 10 mg/kg.

For evaluation of climbing, 3 readings were taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine were discarded.

With full-developed apomorphine climbing, the animals were hanging onto the cage walls, rather motionless, over longer periods of time. By contrast, climbs due to mere motor stimulation usually only lasted a few seconds.

The climbing scores were individually totaled (maximal score: 6 per mouse over 3 readings) and the total score of the control group (vehicle intraperitineally—apomorphine subcutaneously) was set to 100%. $ED_{50}$ values with 95% confidence limits were calculated by a Linear Regression Analysis.

| | Results: | |
|---|---|---|
| Compound | Dose (mg/kg) | Activity (% Climbing Score) |
| 10-[β-(dimethylamino)-ethylthio]dibenzo[b,f]-oxepin | 15 | −20 |
| 11-[β-(dimethylamino)-ethylthio]-2-methylthio dibenz[b,f]oxepin | 10 | −18 |
| 2-fluoro-11-[β-dimethylamino)ethylthio]dibenz[b,f]oxepin | 10 | +10 |
| 2-chloro-11-[β-(dimethylamino)ethylthio]dibenz[b,f]-oxepin | 10 | −5 |

References:
Protais, P., Costentin, J. and Schwartz, J.: Climbing behavior induced by apomorphine in mice: A simple test for the study of dopamin receptors in striatum. Psychopharmacol., 50: 1–6, 1976.
Costall, B., Naylor, R. J. and Nohria, V.: Climbing behavior induced by apomorphine in mice: A potent model for the detection of neuroleptic activity. Eur. J. Pharacol., 50: 39–50, 1978.

EXAMPLE 56

Analgesic Activity

Modified D'Amour-Smith Assay (Tail Flick)

METHOD:

Male mice (Charles River: CD-1) from 18–30 grams were used as test subjects. The mouse tails were individually placed on a "Vee" block and, subsequently, a painful stimulus was produced by an intense light beam (Emdie Instrument Co., Louisa, Va.). The subject quickly responds to the noxious stimuli by flicking its tail. The reaction time, the interval between stimulus onset and response, was automatically measured in 1/10-second increments. Prior to drug administration, two control readings of reaction time were measured for each subject with approximately 15 minutes separating the tests. Subjects were discarded if their reaction times in these control tests varied by more than one second or if their inclusion in the study group caused the spread of reaction times to exceed three seconds.

The mean response time ($\bar{x}$) and the standard deviation (SD) of the values were then calculated for each set of control scores. The formula presented below was used to calculate cut-off values (C.O.) for each set of control scores and the average of these C.O. values was used to determine evidence of analgesic activity in subsequent drug testing.

$$\bar{x} + SD(2) = C.O.$$

$\bar{x}$ = Mean control response times for group
SD = Standard deviation of the response times The C.O. value was actually a determination of a reaction time which exceeds the mean by two standard deviations. Any reaction time, in subsequent drug tests, which was greater than the C.O. value, therefore exceeds 95% of a normal Gaussian distribution and was called a "positive response" indicative of analgesic activity. Latency changes were calculated by subtracting the tail flick latency of the average control times from the latency after treatment for each mouse.

Compounds were tested in treatment groups of ten subjects and drugs, prepared in distilled water, were generally administered subcutaneously (s.c.) in volumes equivalent to 10 cc/kg. The initial testing was usually in the form of a time response at intervals of 15, 30, 45 and 60 minutes after dosing. If analgesic activity was still increasing at 60 minutes, then two additional groups were tested at 90 minute and 120 minute post dosing.

A time response indicated the period of greatest analgesic effect after dosing. Percent analgesic activity was calculated in the following manner:

$$\frac{\% \text{ Positive for Drug Grp.} - \% \text{ Positive for Veh. Control Grp.} \times 100}{100 - \% \text{ Positive for Vehicle Control Group}}$$

The $ED_{50}$ was determined at the peak time of drug activity. A minimum of three dose groups were employed. Drugs were administered in a randomized manner. $ED_{50}$'s were calculated using Litchfield-Wilcoxon (LITWL on PDP II) computer analysis.

Grp. = Group
Veh. = Vehicle

RESULTS:

| Compound | Dose (mg/kg) | Analgesic Activity (%) |
|---|---|---|
| 10-[β-(dimethylamino)ethylthio]dibenzo[b,f]oxepin | 25 | 30 |
| 11-[β-(dimethylamino)ethylthio]-2-methylthio dibenz[b,f]oxepin | 14.1 | 50 |
| 2-fluoro-11-[β-dimethylamino)ethylthio]dibenz[b,f]oxepin | 23.9 | 50 |
| 2-chloro-11-[β-(dimethylamino)ethylthio]dibenz[b,f]oxepin | 25 | 20 |
| 10-[β-(methylamino)ethylthio]dibenzo[b,f]oxepin | 11.6 | 50 |
| 2-fluoro-11-[β-methylamino)ethylthio]dibenz[b,f]oxepin | 11.3 | 50 |

REFERENCE:
(1) D'Amour, Fred and Smith, Donn. J. Pharmacol. Exptl. Therap. 72: 74–79 (1941).

EXAMPLE 57

Stability Study

Gas Chromatographic Assay

METHOD:

Gas chromatographic conditions were established under which 2-fluoro-11-[β-(dimethylamino)ethoxy]-dibenz[b,f]oxepin (as the hydrobromide or hydrochloride salts), 2-fluoro-11-]β-dimethylamino)ethylthio)-dibenz[b,f]oxepin (as the hydrobromide salt) and 10,11-dihydro-10-oxodibenz[b,f]oxepin were separated:
Column—Glass 2 m×2 mm ID packed with 3% OV-225 on 80/100 supelcoport
Temperature: Isothermal at 220° C.
Flow Rate: He at 45 ml/min
Detection: FID
Instrument: Perkin-Elmer 3920B Solutions of 2-fluoro-11-[β-(dimethylamino)ethoxy]-dibenz[b,f]oxepin and 2-fluoro-11-[β-(dimethylamino)ethylthio]dibenz[b,f]oxepin were prepared in water at a concentration of 200 mg/100 ml. Portions of these stock aqueous solutions were used in each of the following experiments. All aqueous samples were prepared for gas chromatographic (GC) injection by first adding sodium carbonate solution to adjust the pH to 9 and then extracting with ethyl acetate. The ethyl acetate layer was separated and 2.0 μl of it were injected.

I. Reflux of 25 ml of 2-fluoro-11-[β-(dimethylamino)ethoxy]dibenz[b,f]oxepin stock solution produced no apparent decomposition after 45 minutes. Addition of 2.5 ml of concentrated hydrochloric acid and further reflux for 10 mins gave complete decomposition to 10,11-dihydro-10-oxodibenz[b,f]oxepin.

II. Acidification of 2.0 ml of 2-fluoro-11-[β-(dimethylamino)ethoxy]dibenz[b,f]oxepin stock solution with 0.2 ml of concentrated hydrochloric acid and standing at ambient temperature produced increases in the levels of 10,11-dihydro-10-oxodibenz[b,f]oxepin beyond the 0.2% level initially contaminating the sample of 2-fluoro-11-[β-(dimethylamino)ethoxy]dibenz[b,f]oxepin.

| Time (min.) | % Increase in decomposition product |
|---|---|
| 2 | 0.35 |
| 60 | 2.16 |
| 140 | 3.00 |

III. Simultaneous experiments were performed using 2.0 ml of each stock solution of 2-fluoro-11-[β-(dimethylamino)ethoxy]dibenz[b,f]oxepin and 2-fluoro-11-[β-(dimethylamino)ethylthio]dibenz[b,f]oxepin in individual test tubes. Acidification of each solution with 0.2 ml of concentrated hydrochloric acid and side by side warming (not reflux) for 2 minutes (electric heat gun) produced a visible change. The 2-fluoro-11-[β-(dimethylamino)ethoxy]dibenz[b,f]oxepin solution became white and cloudy while the 2-fluoro-11-[β-(dimethylamino)ethylthio]dibenz[b,f]oxepin solution remained clear and colorless. GC analysis showed that the 2-fluoro-11-[β-(dimethylamino)ethylthio]dibenz[b,f]oxepin did not decompose. GC analysis showed that 87.2% of 2-fluoro-11-[β-(dimethylamino)ethoxy]-dibenz[b,f]oxepin had decomposed to 10,11-dihydro-10-oxodibenz[b,f]oxepin.

We claim:

1. A compound of the formula

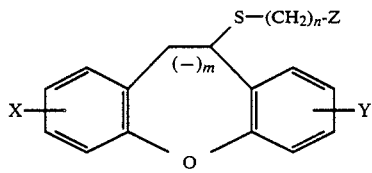

wherein X and Y are the same or different and each can be hydrogen, halogen, trifluoromethyl, loweralkoxy, loweralkyl, loweralkylthio, loweralkylsulfonyl, loweralkylsulfinyl, amino, or nitro; Z is

$R^1$ is hydrogen, straight or branched chain loweralkyl, cyano, cycloalkylloweralkyl wherein the cycloalkyl ring contains from 3 to 6 carbon atoms, phenoxycarbonyl of the formula

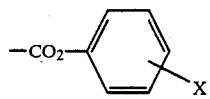

where X is defined as above, alkoxycarbonyl, loweralkenyl or loweralkynyl; $R^2$ is straight or branched chain loweralkyl or cycloalkylloweralkyl wherein the cycloalkyl ring contains from 3 to 6 carbon atoms, phenylethyl of the formula

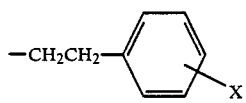

wherein X is defined as above, loweralkenyl or loweralkynyl; and where $R^1$ and $R^2$ are taken together with the nitrogen atom to which they are attached, the group R$^1$—N—R$^2$ forms a heterocycle which is morpholino, piperidino, 4-substituted piperidino in which the 4-substituent is benzoyl of the formula

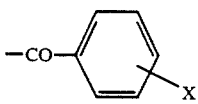

wherein X is defined as above, pyrrolidinyl, piperazinyl or N-substituted piperazinyl in which the N-substituent is loweralkyl; m is the integer 0; and n is an integer of from 2 to 4; and physiologically tolerable acid addition salts thereof.

2. A compound as defined in claim 1 wherein R$^1$ is hydrogen, straight or branched chain loweralkyl and R$^2$ is straight or branched chain loweralkyl.

3. A compound as defined in claim 1 wherein n is 2 and X is hydrogen and Y is hydrogen, halogen or SCH$_3$.

4. A compound as defined in claim 1 wherein n is 2 and X is hydrogen and Y is SO$_2$CH$_3$.

5. The compound defined in claim 1 which is 10,11-dihydro-10-[(β-dimethylamino)ethylthio]dibenz[b,f]oxepin and a physiologically tolerable acid addition salt thereof.

6. The compound defined in claim 1 which is 2-chloro-10,11-dihydro-11-[(β-dimethylamino)ethylthio]-dibenz[b,f]oxepin and a physiologically tolerable acid addition salt thereof.

7. The compound defined in claim 1 which is 2-fluoro-10,11-dihydro-11-[β-(dimethylamino)ethylthio]-dibenz[b,f]oxepin and a physiologically tolerable acid addition salt thereof.

8. The compound defined in claim 1 which is 10,11-dihydro-11-[β-(methylamino)ethylthio]-2-methylthiodibenz[b,f]oxepin and a physiologically tolerable acid addition salt thereof.

9. The compound defined in claim 1 which is 10,11-dihydro-10-[β-(methylamino)ethylthio]dibenz[b,f]oxepin and a physiologically tolerable acid addition salt thereof.

10. The compound defined in claim 1 which is 2-chloro-10,11-dihydro-11-[β-(methylamino)ethylthio]-dibenz[b,f]oxepin and a physiologically tolerable acid addition salt thereof.

11. The compound defined in claim 1 which is 2-fluoro-10,11-dihydro-11-[β-(methylamino)ethylthio]-dibenz[b,f]oxepin and a physiologically tolerable acid addition salt thereof.

12. The compound defined in claim 1 which is 10-[β-(diethylamino)ethylthio]-10,11-dihydrodibenz[b,f]oxepin and a physiologically tolerable acid addition salt thereof.

13. The compound defined in claim 1 which is 10,11-dihydro-10-[β-(4-methylpiperazin-1-yl)ethylthio]-dibenz[b,f]oxepin and a physiologically tolerable acid addition salt thereof.

14. The compound defined in claim 1 which is 10,11-dihydro-10-(β-morpholinoethylthio)dibenz[b,f]oxepin and a physiologically tolerable acid addition salt thereof.

15. The compound defined in claim 1 which is 2-chloro-11-[β-(diethylamino)ethylthio]-10,11-dihydrodibenz[b,f]oxepin and a physiologically tolerable acid addition salt thereof.

16. The compound defined in claim 1 which is 10,11-dihydro-10-[γ-(dimethylamino)propylthio]dibenz[b,f]oxepin and a physiologically tolerable acid addition salt thereof.

17. The compound defined in claim 1 which is 10-[β-(ethylamino)ethylthio]-10,11-dihydrodibenz[b,f]oxepin and a physiologically tolerable acid addition salt thereof.

18. The compound defined in claim 1 which is 11-[β-(diethylamino)ethylthio]-10,11-dihydro-2-(methylthio)-dibenz[b,f]oxepin and a physiologically tolerable acid addition salt thereof.

19. The compound defined in claim 1 which is 10,11-dihydro-11-[β-(dimethylamino)ethylthio]-2-(methylthio)dibenz[b,f]oxepin and a physiologically tolerable acid addition salt thereof.

20. The compound defined in claim 1 which is 10-{β-[4-(4-fluorobenzoyl)-1-piperidinyl]ethylthio}-10,11-dihydrodibenz[b,f]oxepin and a physiologically tolerable acid addition salt thereof.

21. The compound defined in claim 1 which is 10,11-dihydro-10-[β-(4-methylpiperazin-1-yl)ethylthio]-dibenz[b,f]oxepin and a physiologically tolerable acid addition salt thereof.

22. The compound defined in claim 1 which is 11-[β-(allylamino)ethylthio]-2-fluoro-10,11-dihydrodibenz[b,f]oxepin and a physiologically tolerable acid addition salt thereof.

23. The compound defined in claim 1 which is 2-fluoro-10,11-dihydro-11-[β(2-phenylethylamino)ethylthio]dibenz[b,f]oxepin and a physiologically tolerable acid addition salt thereof.

24. The compound defined in claim 1 which is 10,11-dihydro-10-[β-2-(phenylethylamino)ethylthio]-dibenz[b,f]oxepin and a physiologically tolerable acid addition salt thereof.

25. The compound defined in claim 1 which is 11-[β-cyclopropylmethylamino)ethylthio]-2-fluoro-10,11-dihydrodibenz[b,f]oxepin and a physiologically tolerable acid addition salt thereof.

26. The compound defined in claim 1 which is 10,11-dihydro-10-[β-(piperidino)ethylthio]dibenz[b,f]oxepin and a physiologically tolerable acid addition salt thereof.

27. The compound defined in claim 1 which is 10,11-dihydro-10-[γ-(piperazinyl)propylthio]dibenz[b,f]oxepin and a physiologically tolerable acid addition salt thereof.

28. The compound defined in claim 1 which is 10,11-dihydro-10-[γ-(piperidino)-n-butylthio]dibenz[b,f]oxepin and a physiologically tolerable acid addition salt thereof.

29. The compound defined in claim 1 which is 10-[β-(pyrrolidino)ethylthio]dibenz[b,f]oxepin and a physiologically tolerable acid addition salt thereof.

30. The compound defined in claim 1 which is 10-[β-(ethylamino)ethylthio]-10,11-dihydro-4-nitrodibenz[b,f]oxepin and a physiologically tolerable acid addition salt thereof.

31. The compound defined in claim 1 which is 8-chloro-10,11-dihydro-10-[β-(dimethylamino)ethylthio]-2-methyldibenz[b,f]oxepin and a physiologically tolerable acid addition salt thereof.

32. A method of treating depression which comprises administering to a patient a pharmaceutically effective amount of a compound defined in claim 1.

33. A method of treating pain which comprises administering to a patient a pharmaceutically effective amount of a compound defined in claim 1.

34. A method of treating convulsions which comprises administering to a patient a pharmaceutically effective amount of a compound defined in claim 1.

35. A pharmaceutical composition which comprises between 0.5 and about 70% by weight of a compound defined in claim 1 and a pharmaceutically acceptable carrier therefor.

36. A method of treating depression which comprises administering to a patient a pharmaceutically effective amount of a compound defined in claim 3.

37. A method of treating pain which comprises administering to a patient a pharmaceutically effective amount of a compound defined in claim 3.

38. A method of treating convulsions which comprises administering to a patient a pharmaceutically effective amount of a compound defined in claim 3.

39. A pharmaceutical composition which comprises between 0.5 and about 70% by weight of a compound defined in claim 13 and a pharmaceutically acceptable carrier therefor.

* * * * *